United States Patent
Li et al.

(10) Patent No.: US 12,318,619 B2
(45) Date of Patent: Jun. 3, 2025

(54) MEDICAL LEADS AND TECHNIQUES FOR MANUFACTURING THE SAME

(71) Applicant: Medtronic, Inc., Minneapolis, MN (US)

(72) Inventors: Bernard Q. Li, Plymouth, MN (US); Richard T. Stone, Roseville, MN (US); Alan Shi, Plymouth, MN (US); Seth M. Humphrys, Golden Valley, MN (US); Wen Tan, Shoreview, MN (US); Nicholas D. Stepka, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 393 days.

(21) Appl. No.: 17/663,601

(22) Filed: May 16, 2022

(65) Prior Publication Data

US 2022/0379121 A1    Dec. 1, 2022

Related U.S. Application Data

(60) Provisional application No. 63/193,997, filed on May 27, 2021.

(51) Int. Cl.
*A61N 1/375* (2006.01)
*C22C 14/00* (2006.01)
*C22F 1/18* (2006.01)

(52) U.S. Cl.
CPC .............. *A61N 1/375* (2013.01); *C22C 14/00* (2013.01); *C22F 1/183* (2013.01)

(58) Field of Classification Search
CPC ....... C22C 14/00; C22F 1/183; A61N 1/0551; A61N 1/0529
See application file for complete search history.

(56) References Cited

U.S. PATENT DOCUMENTS

| 4,542,752 A | 9/1985 | DeHaan et al. |
| 8,340,759 B2 | 12/2012 | McIntyre et al. |

(Continued)

FOREIGN PATENT DOCUMENTS

| CN | 109091754 A | 12/2018 |
| JP | 2012052143 A | 3/2012 |

(Continued)

OTHER PUBLICATIONS

Notice of Intent to Grant and Text Intended to Grant from counterpart European Application No. 22175301.5 dated Jul. 3, 2023, 101 pp.

(Continued)

*Primary Examiner* — Paula J Stice
(74) *Attorney, Agent, or Firm* — Shumaker & Sieffert, P.A.

(57) ABSTRACT

In some examples, the disclosure relates to a medical device such as an implantable medical lead. The medical lead may include: a lead body including an electrically conductive lead wire; an electrical contact on a proximal portion of the lead body, the electrical contact including a contact substrate; and an electrode on a distal portion of the lead body, the electrode including an electrode substrate, wherein the electrode substrate is electrically coupled to the contact substrate via the electrically conductive lead wire, wherein the lead wire is formed of a composition comprising titanium or titanium alloys, wherein the electrode substrate is formed of a first beta-titanium alloy, and wherein the contact substrate is formed of a second beta-titanium alloy.

18 Claims, 13 Drawing Sheets

(56) References Cited

U.S. PATENT DOCUMENTS

| | | |
|---|---|---|
| 8,843,214 B2 | 9/2014 | Li et al. |
| 9,283,372 B2 | 3/2016 | Bondhus et al. |
| 9,694,173 B2 | 7/2017 | Li et al. |
| 9,752,214 B2 | 9/2017 | Takeguchi et al. |
| 10,406,349 B2 | 9/2019 | Shi et al. |
| 10,583,217 B2 | 3/2020 | Ishikawa et al. |
| 10,669,613 B2 | 6/2020 | Takeguchi et al. |
| 2010/0256718 A1 | 10/2010 | Wang et al. |
| 2013/0138186 A1 | 5/2013 | Iyer et al. |
| 2014/0343644 A1* | 11/2014 | Shi ............ A61N 1/05 607/116 |
| 2017/0281269 A1 | 10/2017 | Ishikawa et al. |
| 2019/0008605 A1 | 1/2019 | Matsushima et al. |
| 2019/0060636 A1 | 2/2019 | Steigauf et al. |
| 2019/0269929 A1* | 9/2019 | Bjorklund .......... A61N 1/37512 |
| 2019/0358021 A1 | 11/2019 | Kubo et al. |
| 2021/0085957 A1* | 3/2021 | Foster .............. A61N 1/05 |
| 2021/0161471 A1 | 6/2021 | Lima De Miranda |

FOREIGN PATENT DOCUMENTS

| | | |
|---|---|---|
| JP | 2017006837 A | 1/2017 |
| JP | 2018001349 A | 1/2018 |

OTHER PUBLICATIONS

Response to Extended Search Report dated Nov. 3, 2022, from counterpart European Application No. 22175301.5 filed May 5, 2023, 1 pp.

Extended Search Report from counterpart European Application No. 22175301.5 dated Nov. 3, 2022, 5 pp.

Results for "Nippon Piston Ring Co., Ltd." on IPowner Patents & Trademarks, accessed from https://www.onscope.com/ipowner/en/owner/ip/957797-nippon-piston-ring-co-ltd.html, accessed on Dec. 9, 2022, 112 pp.

* cited by examiner

MEDICAL LEADS AND TECHNIQUES FOR MANUFACTURING THE SAME

This application claims the benefit of U.S. Provisional Patent Application No. 63/193,997, filed May 27, 2021, the entire content of which is incorporated herein by reference.

TECHNICAL FIELD

The present disclosure relates to medical devices, more particularly to medical device leads configured for delivery of electrical stimulation therapy and/or sensing of electrical signals using one or more electrodes.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. In some cases, implantable electrodes may be coupled to an external electrical stimulation generator via one or more percutaneous leads or fully implanted leads.

SUMMARY

Some examples of the present disclosure relate to medical device leads including one or more electrodes for use in medical device systems. For example, a distally located electrode may be electrically coupled to a corresponding electrical contact at the proximal portion of the lead body by a lead wire in the lead body. The electrical contact may be configured to connect directly or indirectly (e.g., via a lead extension) to an electrical stimulation generator of a medical device such as an implantable medical device (IMD) so that electrical signals may be conducted from the stimulation generator to the electrode, e.g., for delivery of electrical stimulation to a patient. Additionally, or alternatively, the electrode may be electrically coupled to sensing circuitry in the IMD via the lead wire and electrical contact for sensing of electrical signals using the electrode.

The electrical contact substrate may be formed of a material including a first beta titanium alloy (e.g., a Ti-15Mo alloy) and the electrode substrate may be formed of a material including a second beta titanium alloy (e.g., a TiTaSn alloy such as a Ti alloy with about 46 weight percent (wt %) to about 54 wt % Ta and about 3.5 wt % to about 6.5 wt % Sn). The lead wire may be formed of titanium or a titanium alloy (e.g., a third beta titanium alloy), which may be the same or different composition compared to that of the electrical contact substrate and/or the electrode substrate. In some examples, the lead wire, electrode, and electrical contact may each be formed of a beta titanium alloy (e.g., two or more beta Ti alloys having different alloying elements and/or amounts of alloying elements). The lead wire may be connected to the electrode substrate and contact substrate by a weld (e.g., a laser weld or resistance weld). In some examples, the electrode substrate may be coated with a relatively high surface area coating such as TiN that improves the charge injection capacities of the electrode or may be modified by laser beam to create microscopic/nanoscopic features to increase effective surface area therefore increased charge injection capacity.

In one example, the disclosure relates to a medical lead comprising a lead body including an electrically conductive lead wire; an electrical contact on a proximal portion of the lead body, the electrical contact comprising a contact substrate; and an electrode on a distal portion of the lead body, the electrode comprising an electrode substrate, wherein the electrode substrate is electrically coupled to the contact substrate via the electrically conductive lead wire, wherein the lead wire is formed of a composition comprising titanium or titanium alloys, wherein the electrode substrate is formed of a first beta-titanium alloy, and wherein the contact substrate is formed of a second beta-titanium alloy.

In another example, the disclosure relates to a method for assembling a medical lead, the assembled medical lead comprising a lead body including an electrically conductive lead wire; an electrical contact on a proximal portion of the lead body, the electrical contact comprising a contact substrate; and an electrode on a distal portion of the lead body, the electrode comprising an electrode substrate, the method comprising: attaching the lead wire to the electrode substrate; and attaching the lead wire to the contact substrate to electrically couple the electrode substrate to the contact substrate via the electrically conductive lead wire, wherein the lead wire is formed of a composition comprising titanium or titanium alloys, wherein the electrode substrate is formed of a first beta-titanium alloy, and wherein the contact substrate is formed of a second beta-titanium alloy.

The details of one or more aspects of the disclosure are set forth in the accompanying drawings and the description below. Other features, objects, and advantages will be apparent from the description and drawings, and from the claims.

DETAILED DESCRIPTION

Figure 1:
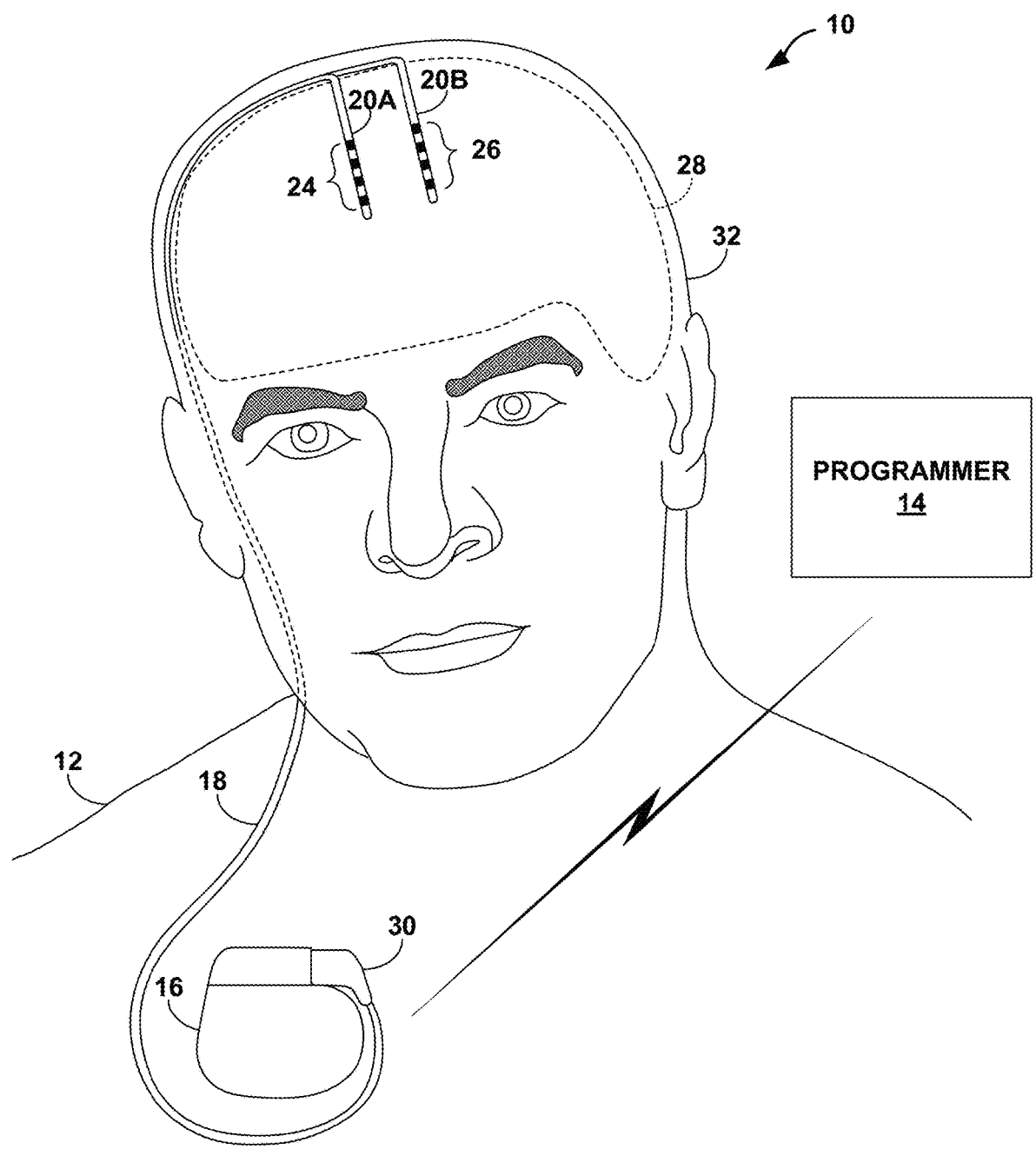
FIG. 1 is a conceptual diagram illustrating an example medical device system.

As described above, some examples of the disclosure relate to medical device leads (also referred to as "medical leads" or "leads") including one or more electrodes, e.g., on a distal portion of a lead each with a corresponding electrical contact on the proximal portion of the lead. A medical lead may be implanted within a patient and, using the lead, a medical device may deliver and/or sense electrical signals to provide therapy to a patient to treat a patient condition. The electrodes may each include a conductive electrode substrate electrically and mechanically connected to one or more conductive lead wires extending through the lead body to the corresponding electrical contact. Electrical stimulation from a medical device may be conductive via the electrical contact and lead wire to the electrode substrate to be delivered across the electrode surface.

In some examples, an implantable medical lead may include a conductive lead wire formed of a cobalt based (CoNiCrMo) alloy such as MP35N® with an electrical contact of the same material and an electrode formed of a platinum (Pt) composition such as platinum iridium. The Pt alloy electrode and MP35N® alloy electrical contact may be electrically and mechanically coupled to the MP35N® alloy lead wire via lasing welding.

However, in some instances, it may be desirable to employ a lead wire formed of a titanium alloy composition such as Ti-15Mo. For example, for vagus nerve and other peripheral nerve stimulation, a titanium alloy lead wire may provide for improved fatigue endurance, flexibility, and/or axial extensibility compared to that of some cobalt based alloy lead wires. A titanium alloy lead wire may provide for desirable properties in a medical lead in terms of high flexibility, high axial extensibility, and/or high fatigue resistance, but laser welding a titanium alloy lead wire to a Pt alloy electrode or cobalt based alloy electrical contact can be difficult. For example, micro cracking may occur in an intermetallic layer when a titanium alloy lead wire and Pt alloy electrode are welded together, which may impose a reliability concern. Likewise, a MP35N® electrical contact may not be weldable to a Ti alloy lead wire. While different compositions may provide for better weldability to a titanium alloy lead wire, in some examples, such compositions do not necessarily provide for radiopacity at a level described for electrodes for implantable medical leads.

In accordance with examples of the disclosure, medical lead designs include a lead wire formed of a titanium alloy composition such as Ti-15Mo alloy, an electrode formed of a beta titanium alloy composition, and an electrical contact formed of a beta titanium alloy composition. For each of the electrode and electrical contact, the beta titanium alloy may include titanium and one or more beta stabilizing alloying elements such as Ta, Nb, Mo, Zr, V, Sn. A beta titanium alloy may have a body center cubic (BCC) structure, e.g., in comparison to an alpha titanium alloy which has hexagonal close packed (HCP) structure. The beta titanium alloy(s) used to form the electrode and electrical contact may exhibit a high level of weldability to the Ti alloy lead wire. In some examples, the lead wire may also be formed of a beta titanium alloy composition that is the same or different from the beta titanium alloy composition that forms the electrode and/or electrical contact substrates.

A Ti-15Mo alloy or other titanium alloy composition described herein for the lead wire may provide for relatively high flexibility, high axial extensibility, and/or high fatigue resistance. In some examples, the lead wire may be a Ti-15Mo alloy (or other Ti alloy) lead wire and may be a single or multi-filar coil lead wire. In the case of a lead with multiple electrodes and an electrical contact for each of the multiple electrodes, a respective filar of a multi-filar lead wire may electrically couple each electrode to the corresponding electrical contact. The lead wire may be coated with an electrical insulator such as soluble imide (SI) polyimide, e.g., with each filar being coated with an insulator to electrically isolate respective filars from each other and/or with the lead wire in total being coated to electrically isolate the lead wire from the surrounding environment.

In some examples, the beta titanium alloy composition for the electrode may be selected to provide radiopacity, welding, and/or formability properties. As described below, in some examples, a TiTaSn alloy (e.g., an TiTaSn alloy with about 46 wt % to about 54 wt % Ta and about 3.5 wt % to about 6.5 wt % Sn and the remainder Ti) may be used to form an electrode substrate. Such a composition may be weldable to a Ti-15Mo lead wire, may have a desirable level of radiopacity, and/or may be formable as an electrode substrate in the manner desired for an implantable medical lead. As used herein, formable may refer to the ability of a material to be cold worked to form different shapes such as a wire, tube, rod, and strip, as described herein. An electrode substrate formed with the beta titanium composition may have any suitable shape such as a tubular ring, half ring or flat paddle shape. The electrode may be welded (e.g., laser welded or resistance welded) to the lead wire. In some examples, the electrode surface may be coated with a high surface area coating (e.g., to define a fractal surface with surface geometry features for a high surface area) such as TiN to improve charge injection capacity of the electrode or may be modified by laser beam to create microscopic/nanoscopic features to increase effective surface area therefore increased charge injection capacity. Other examples coatings may include fractal Pt, fractal graphene, conductive poly(3,4-ethylenedioxythiophene) (PEDOT), or the like.

The beta titanium alloy composition for the electrical contact on the proximal end of the lead may be the same or different from that of the electrode composition. In examples in which the beta titanium alloy composition of the electrical contact is different than the electrode, the beta titanium composition of the electrical contact may include different alloying elements, different concentrations of alloying elements, and/or different concentrations of beta phase as compared to the electrode. In some examples, the electrical contact may be formed of a beta titanium alloy including alloying elements such as Mo, Nb, Ta, Nb, Zr, Al, and/or the like. In some examples, the electrical contact is formed of an alloy such as Ti-15Mo, Ti15Mo5Zr3Al, Ti29Nb13Ta5Zr (TNTZ) or the like. The beta titanium alloy of the electrical contact may be selected to tolerate relatively high hydrogen (H) content (e.g., a H content of about 300 parts per million or greater), e.g., without embrittlement of the wire due to the H content. The electrical contact may have a ring shape although other shapes are contemplated.

Like that of the attachment between the electrode and lead wire, the electrical contact may be welded (e.g., laser welded or resistance welded) to the lead wire. In some examples, a lead may include a lead wire formed of a Ti-15Mo alloy that is welded to a TiTaSn alloy electrode on the distal end and also welded to a Ti-15Mo alloy electrical contact on the proximal end.

FIG. 1 is a conceptual diagram illustrating an example therapy system 10 with a stimulation lead implanted in the brain of a patient. Therapy system 10 includes medical device programmer 14, implantable medical device (IMD) 16, lead extension 18, and one or more leads 20A and 20B (collectively "leads 20") with respective sets of electrodes 24, 26. IMD 16 includes a stimulation therapy module that includes an electrical stimulation generator that generates and delivers electrical stimulation therapy to one or more regions of brain 28 of patient 12 via a subset of electrodes 24, 26 of leads 20A and 20B, respectively. In the example shown in FIG. 1, therapy system 10 may be referred to as a DBS system because IMD 16 provides electrical stimulation therapy directly to tissue within brain 28, e.g., a tissue site under the dura mater of brain 28. In other examples, leads 20 may be positioned to deliver therapy to a surface of brain 28 (e.g., the cortical surface of brain 28).

For ease of illustration, examples of the disclosure will primarily be described with regard to implantable electrical stimulation leads and implantable medical devices that neurostimulation therapy to a patient's brain in the form of DBS. However, the features and techniques described herein may be useful in other types of medical device systems, which may include other types of implantable medical leads for use with medical devices, such as, e.g., implantable medical devices (IMDs). For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation, vagus nerve stimulation, or sacral nerve stimulation), stimulation of at least one muscle or muscle groups, stimulation of at least one organ such as gastric system stimulation, stimulation concomitant to gene therapy, and, in general, stimulation of any tissue of a patient. In some examples, the features and techniques described herein may be used in systems with medical devices that deliver peripheral nerve stimulation therapy or peripheral nerve field stimulation therapy.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. Generally, IMD 16 is constructed of a biocompatible material that resists corrosion and degradation from bodily fluids. IMD 16 may comprise a hermetic housing 34 to substantially enclose components, such as a processor, therapy module, and memory.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Although FIG. 1 illustrates system 10 as including two leads 20A and 20B coupled to IMD 16 via lead extension 18, in some examples, system 10 may include one lead or more than two leads.

Leads 20 may deliver electrical stimulation via electrodes 24, 26 to treat any number of neurological disorders or diseases in addition to movement disorders, such as seizure disorders or psychiatric disorders. Leads 20 may be implanted within a desired location of brain 28 via any suitable technique, such as through respective burr holes in a skull of patient 12 or through a common burr hole in the cranium 32. Leads 20 may be placed at any location within brain 28 such that electrodes 24, 26 of leads 20 are capable of providing electrical stimulation to targeted tissue during treatment. In the examples shown in FIG. 1, electrodes 24, 26 of leads 20 are shown as ring electrodes. In other examples, electrodes 24, 26 of leads 20 may have different configurations including segmented electrodes or paddle electrodes. Electrodes 24, 26 of leads 20 may have a complex electrode array geometry that is capable of producing shaped electrical fields. In this manner, electrical stimulation may be directed to a specific direction from leads 20 to enhance therapy efficacy and reduce possible adverse side effects from stimulating a large volume of tissue.

In accordance with one or more examples of the disclosure, electrodes 24 and 26 may include an electrode substrate formed of a beta titanium alloy. In some examples, the beta titanium alloy may be a TiTaSn alloy such as Ti50Ta4Sn. Each of electrodes 24 and 26 may be electrically coupled to a respective lead wire (not shown in FIG. 1) extending from electrodes 24 and 26 to a corresponding electrical contact (not shown in FIG. 1) on the distal portion of lead 20. The lead wires may be electrically insulated from each other to electrically isolate electrode 24 from electrode 26. The lead wires may be formed of a titanium alloy and may be coated with an electrical insulator. The titanium alloy for the lead wire may exhibit relatively high flexibility, high axial extensibility, and/or high fatigue resistance. The electrical contacts may include a contact substrate formed of a beta titanium alloy that is the same or different from that of electrodes 24 and 26. A distal portion of each lead wire may be welded to one of electrodes 24 and 26 on a distal portion of leads 20 and a proximal portion of each lead wire may be welded to the corresponding electrical contact as the proximal portion of leads 20.

IMD 16 may deliver electrical stimulation therapy to brain 28 of patient 12 according to one or more stimulation therapy programs. A therapy program may define one or more electrical stimulation parameter values for therapy generated and delivered from IMD 16 to brain 28 of patient 12. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 12, therapy system 10 monitors one or more bioelectrical brain signals of patient 12. For example, IMD 16 may include a sensing module that senses bioelectrical brain signals within one or more regions of brain 28. In the example shown in FIG. 1, the signals generated by electrodes 24, 26 are conducted to the sensing module within IMD 16 via conductors within the respective lead 20A, 20B. As described in further detail below, in some examples, a processor of IMD 16 may sense the bioelectrical signals within brain 28 of patient 12 and controls delivery of electrical stimulation therapy to brain 28 via electrodes 24, 26.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14.

Figure 2:
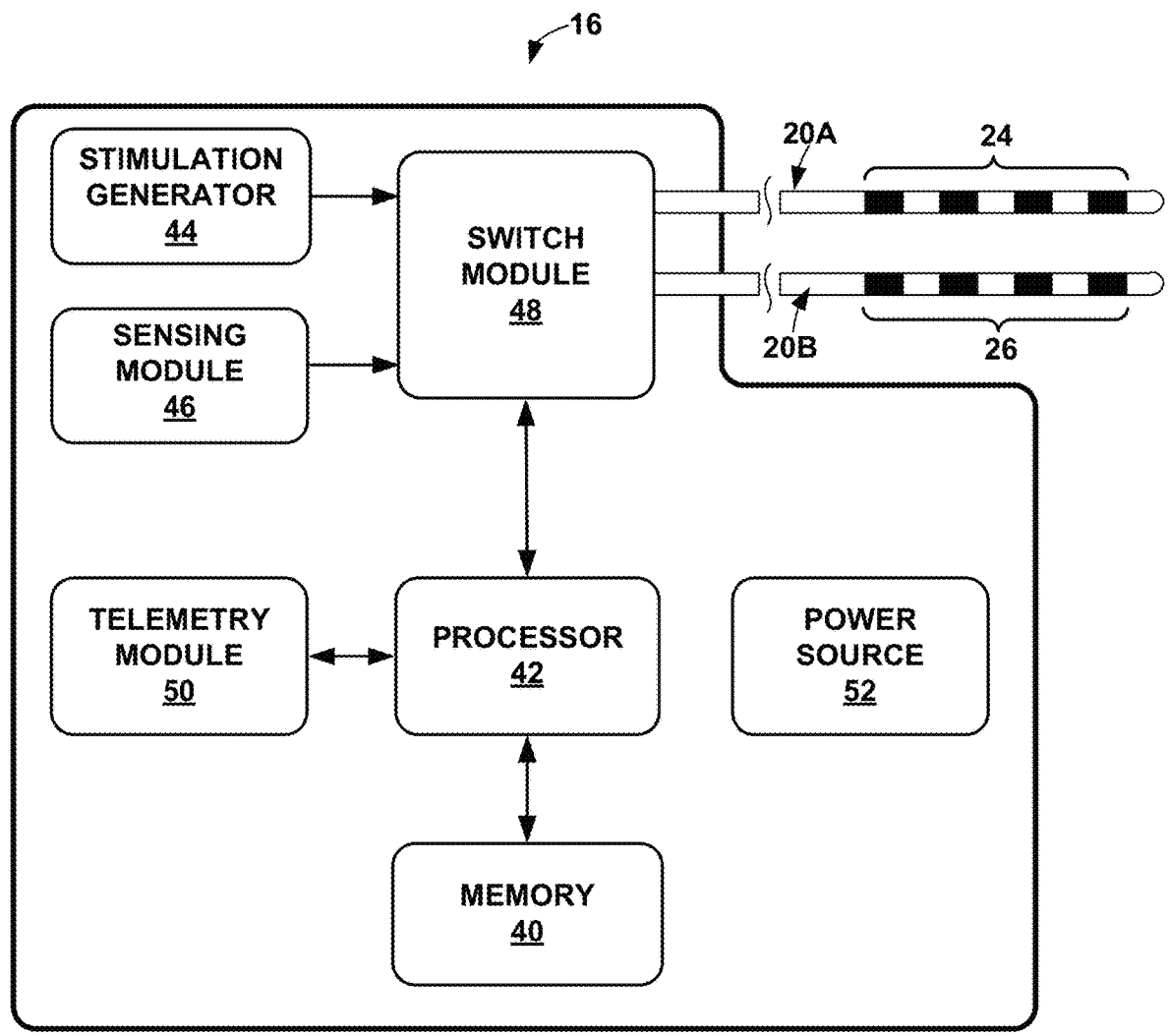
FIG. 2 is a conceptual diagram illustrating an example implantable medical device.

FIG. 2 is a functional block diagram illustrating components of IMD 16. In the example shown in FIG. 2, IMD 16 includes memory 40, processor 42, stimulation generator 44, sensing module 46, switch module 48, telemetry module 50, and power source 52. Processor 42 may include processing circuitry including any one or more microprocessors, controllers, digital signal processors (DSPs), application specific integrated circuits (ASICs), field-programmable gate arrays (FPGAs), and discrete logic circuitry. The functions attributed to processors described herein, including processor 42, may be provided by a hardware device and embodied as software, firmware, hardware, or any combination thereof.

In the example shown in FIG. 2, sensing module 46 includes sensing circuitry configured to sense bioelectrical brain signals of patient 12 via select combinations of electrodes 24, 26. The output of sensing module 46 may be received by processor 42. In some cases, processor 42 may apply additional processing to the bioelectrical signals, e.g., convert the output to digital values for processing and/or amplify the bioelectrical brain signal. In addition, in some examples, sensing module 46 or processor 42 may filter the signal from the selected electrodes 24, 26 in order to remove undesirable artifacts from the signal, such as noise from cardiac signals generated within the body of patient 12. Although sensing module 46 is incorporated into a common outer housing with stimulation generator 44 and processor 42 in FIG. 2, in other examples, sensing module 46 is in a separate outer housing from the outer housing of IMD 16 and communicates with processor 42 via wired or wireless communication techniques. In some examples, sensing module 46 may sense brain signals substantially at the same time that IMD 16 delivers therapy to patient 14. In other examples, sensing module 46 may sense brain signals and IMD 16 may deliver therapy at different times.

Memory 40 may include any volatile or non-volatile media, such as a random access memory (RAM), read only memory (ROM), non-volatile RAM (NVRAM), electrically erasable programmable ROM (EEPROM), flash memory, and the like. Memory 40 may store computer-readable instructions that, when executed by processor 42, cause IMD 16 to perform various functions described herein. Memory 40 may be, in some examples, a non-transitory computer-readable storage medium comprising instructions that cause one or more processors, such as, e.g., processor 42, to implement one or more of the example techniques described in this disclosure. The term "non-transitory" may indicate that the storage medium is not embodied in a carrier wave or a propagated signal. However, the term "non-transitory" should not be interpreted to mean that memory 40 is non-movable. As one example, memory 40 may be removed from IMD 16, and moved to another device. In certain examples, a non-transitory storage medium may store data that can, over time, change (e.g., in RAM).

In the example shown in FIG. 2, processor 42 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 42 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 22A, 22B and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. In some examples, IMD 16 may include separate current sources and sinks for each individual electrode (e.g., instead of a single stimulation generator) such that switch module 48 may not be necessary.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 may support wireless communication between IMD 16 and an external programmer 14 or another computing device under the control of processor 42. Telemetry module 50 in IMD 16, as well as telemetry modules in other devices and systems described herein, such as programmer 14, may accomplish communication by radiofrequency (RF) communication techniques. In addition, telemetry module 50 may communicate with external programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
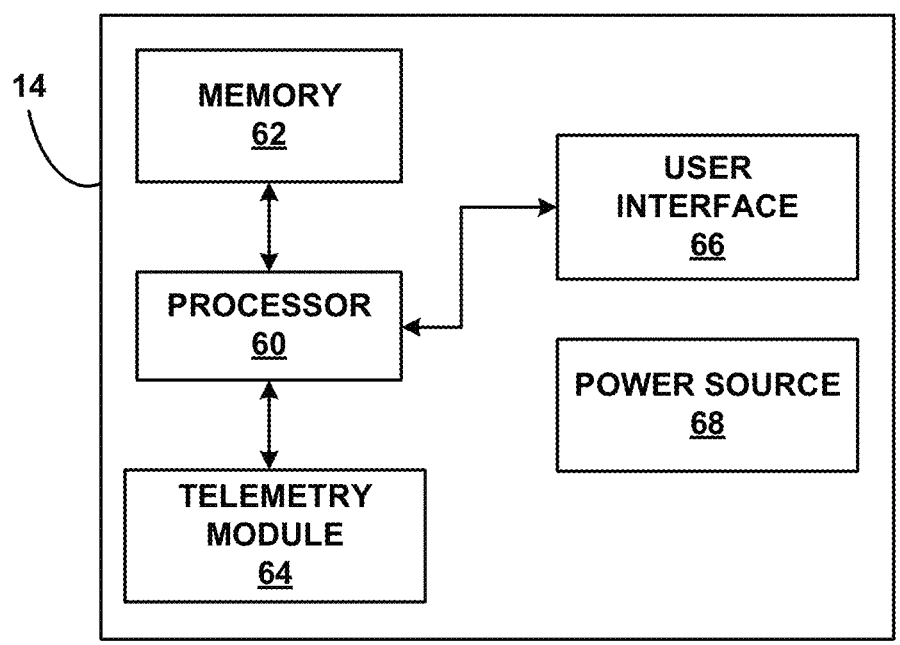
FIG. 3 is a conceptual diagram illustrating an example medical device programmer.

FIG. 3 is a conceptual block diagram of an example external medical device programmer 14, which includes processor 60, memory 62, telemetry module 64, user interface 66, and power source 68. Processor 60 includes processing circuitry that controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

Memory 62 may include instructions for operating user interface 66 and telemetry module 64, and for managing power source 68. Memory 62 may also store any therapy data retrieved from IMD 16 during the course of therapy. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Memory 62 may be considered, in some examples, a non-transitory computer-readable storage medium comprising instructions that cause one or more processors, such as, e.g., processor 60, to implement one or more of the example techniques described in this disclosure. The term "non-transitory" may indicate that the storage medium is not embodied in a carrier wave or a propagated signal. However, the term "non-transitory" should not be interpreted to mean that memory 62 is non-movable. As one example, memory 62 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 may deliver operating power to the components of programmer 14. Power source 68 may include a battery and a power generation circuit to produce the operating power. In some examples, the battery may be rechargeable to allow extended operation.

Figure 4:
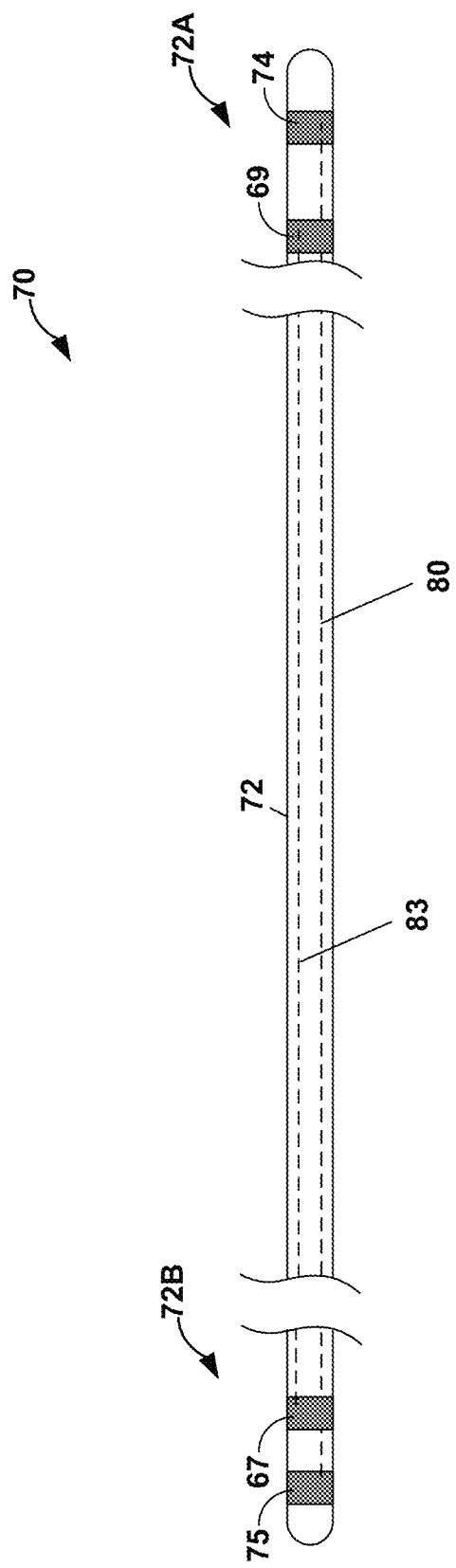
FIG. 4 is a conceptual diagram illustrating an example medical lead.

FIG. 4 is a conceptual diagram illustrating an example medical device lead 70 for use in a medical device system, such as, e.g., medical device system 10 of FIG. 1. Lead 70 may be substantially the same or similar to that of lead 20A or 20B of FIG. 1. For ease of description, lead 70 will be described with regard to system 10 of FIG. 1.

Lead body 72 includes distal portion 72A and proximal portion 72B. As shown, lead 70 includes first ring electrode 74 and second ring electrode 69 located at different axial positions on distal portion 72A of lead body 72. Lead 70 also includes first ring electrical contact 75 and second ring electrical contact 67 located at different axial positions on proximal portion 72B of lead body 72. Lead body 72 is formed at least in part of an electrically insulating, biocompatible material, such as, e.g., polyurethane (polyether urethane or polycarbonate urethane) or silicone, as an outer insulative wall that encloses lead wires 80 and 83 and receives electrodes 69 and 74 and contacts 67 and 75.

Lead body 72 includes first lead wire 80 and second lead wire 83 (represented by the dashed lines). For ease of illustration, lead wires 80 and 83 are shown extending in a linear manner between the distal and proximal portions of lead body 72. In other examples, lead wires 80 and 83 may extend in a coiled configuration (e.g., with each wire running adjacent to each other in a coiled configuration) within lead body 72. FIG. 7D illustrates an example of a multi-filar coiled lead wire 93. The respective lead wires 80 and 83 may be electrically insulated from each other, e.g., in the manner described herein.

First lead wire 80 extends within lead body 72 from first electrode 74 to first electrical contact 75, and electrically couples first electrode 74 to first electrical contact 75. Lead wire 80 may be attached to electrode 74 and electrical contact 75 by any suitable connection including welding, such as resistance welding or laser welding. Electrical signals may be conducted between electrode 74 and electrical contact 75 by lead wire 80. Electrical contact 75 is configured to be electrically coupled to IMD 16 by connector block 30 (e.g., either directly or indirectly via a lead extension) for delivery of electrical stimulation and/or sensing of electrical signals as described herein.

Similarly, second lead wire 83 extends within lead body 72 from second electrode 69 to second electrical contact 67, and electrically couples second electrode 69 to second electrical contact 67. Lead wire 83 may be attached to electrode 69 and electrical contact 67 by any suitable connection including welding, such as resistance welding or laser welding. Electrical signals may be conducted between electrode 69 and electrical contact 67 by lead wire 83. Electrical contact 67 is configured to be electrically coupled to IMD 16 by connector block 30 (e.g., either directly or indirectly via a lead extension) for delivery of electrical stimulation and/or sensing of electrical signals as described herein.

While the example of FIG. 4 illustrates lead 70 as having only two ring electrodes, two lead wires, and two electrical contacts, other examples are contemplated in which lead 70 includes a single electrode/wire/contact or more than two electrodes/wires/contacts. For multiple electrodes, each electrode may be electrically coupled to a separate lead wire and separate electrical contacts so that the electrodes are electrically isolated from each other. Additionally, while the example of FIG. 4 shows electrodes 74 and 69 as ring electrodes where the outer surface of electrodes 74 and 69 extend around the outer circumference of lead body 72, other examples are contemplated. For example, electrode 74 and/or electrode 69 may be a segmented ring electrode (e.g., where the outer surface of the electrode extends only partially around the outer circumference of lead body 72), a paddle electrode, tip electrode or any other desired electrode shape. In the case of segmented electrodes, in one example, multiple electrode segments may be positioned at different circumferential positions around the lead at an axial position of the lead. In some examples, lead may include all ring electrodes, all segmented electrodes, or combinations of one or more ring electrodes and segmented electrodes. Likewise, electrical contacts 75 and 67 are not limited to a ring shape but may be any suitable shape that allows for electrical connection to IMD 16.

When implanted in patient, lead 70 may follow a relatively tortuous, non-linear path from IMD 16 to the target tissue site, including in the case of peripheral nerve stimulation, e.g., at a vagus nerve, wrist, knee, or other locations. Additionally, the movement of patient 12 when lead 70 is implanted may can cause lead 70 to flex or extend periodically and repeatedly. Thus, as described further below, it may be beneficial for lead 70 to be formed of the materials described below so that lead 70 exhibits relatively high fatigue life, low stiffness, and/or high axial extensibility. Such a lead may reduce complicated surgical procedures and allow for new stimulation locations in patient 12.

Figure 5A:
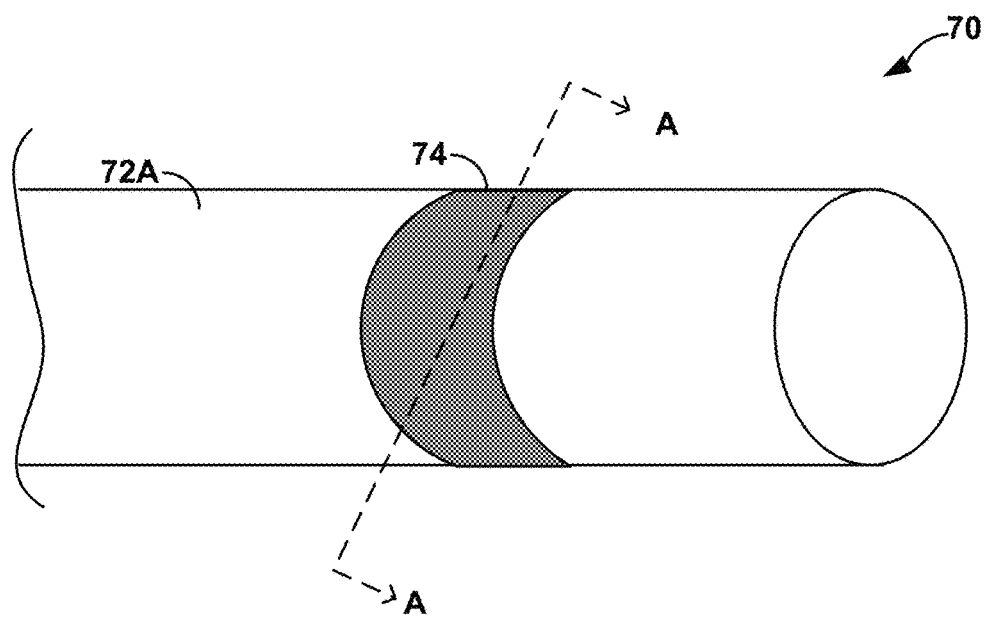
FIG. 5A is a conceptual diagram illustrating the distal portion an example medical device lead including an electrode.
Figure 5B:
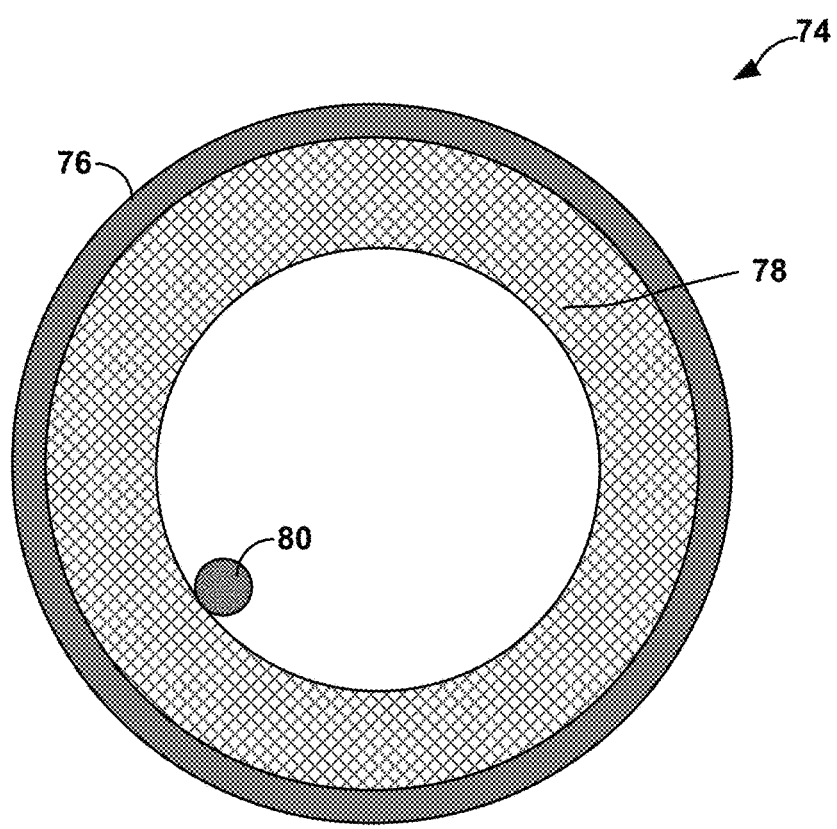
FIG. 5B is a conceptual diagram illustrating the example medical device lead of FIG. 5A along cross-section A-A.

FIG. 5A is a conceptual diagram illustrating a part of distal portion 72A of lead 70 shown in FIG. 4. FIG. 5B is a conceptual diagram illustrating the example medical device lead of FIG. 5A along cross-section A-A. As shown, electrode 74 includes electrode substrate 78 and optional coating 76 deposited on the outer surface of substrate 78. Conversely, the inner surface of substrate 78 is mechanically and electrically coupled to conductive lead wire 80. When implanted in patient 12, the outer surface of optional coating 76 on electrode substrate 78 may interface or be in contact with tissue of patient 12. Electrical stimulation may be delivered to patient 12 via electrode 74 by conducting electrical stimulation current generated by IMD 16 from lead wire 80 across coating 76 via electrode substrate 78. Likewise, for sensing with electrode 74, electrical signals may be transmitted across coating 76 to lead wire 80 via substrate 78 to IMD 16. In examples in which electrode 74 does not include coating 76, the outer surface of electrode substrate 78 may interface or be in contact with the tissue of patient 12 to allow for electrical signals to be conducted between the tissue and electrode substrate 78.

As noted above, lead wire 80 may be formed of a composition including titanium or alloys thereof. The titanium alloy may be a beta titanium alloy, such as, e.g., Ti-15Mo (e.g., a Ti alloy with about 15 wt. % Mo) or other low modulus beta titanium alloys lead wires. In one example, lead wire 80 may be formed of a beta titanium alloy including at least about 90 vol % beta phase, such as at least about 95 vol % beta phase. As noted above, Ti and Ti alloys, and Ti-15Mo alloys in particular, may exhibit superior fatigue life, axial extensibility and/or stiffness, e.g., as compared to that of Pt or Pt—Ir or MP35N® lead wires. For example, a Ti-15Mo alloy or other beta Ti alloy may exhibit approximately twice the fatigue endurance limit and less than about half the modulus of a comparable lead wire formed of MP35N®. Thus, lead wire 80 may exhibit relatively low stiffness, high axial extensibility, and/or high fatigue life, e.g., compared to a lead wire formed of MP35N®. Such properties may allow for lead 70 to endure cyclic movement of lead 70, e.g., when lead 70 extends from IMD 16 to a vagus nerve or other peripheral nerve location of patient 12. In the case of a four filar coiled lead wire formed of MP35N® that has an extensibility fatigue limit at about 12%, a similar four filar coiled lead with same geometry but formed of Ti-15Mo may have an extensibility fatigue limit at about 24%.

Example alloying elements for a Ti alloy used to form lead wire 80 may include one or a combination of Mo, Nb, Ta, Zr, Fe, Sn, Fe and Al. In one example, lead wire 80 is formed of a Ti—Mo alloy, e.g., wherein Mo is present in between about 5 wt % to about 25 wt %. In some examples, the Ti—Mo alloy may include one or more additional alloying elements or may only include Ti—Mo in the alloy composition (e.g., about 5 wt % to about 25 wt % Mo with a remainder being Ti). In one example, lead wire 80 may consist essentially of a titanium alloyed with one or more elements, where any additional material is present only in an amount that does not alter one or more properties of the material in a manner that prevents lead 70 from functioning as described herein. In one example, the H content in the composition used for lead wire 80 may be about 300 ppm or more, e.g., without embrittlement due to the H content as may be observed with some other titanium alloys such as alpha titanium alloys.

Lead wire 80 may be a unitary structure formed of a substantially uniform Ti alloy composition such as Ti-15Mo. In some examples, lead wire 80 may be a single unitary component with a substantially uniform composition such as a single filar wire. In other examples, lead wire 80 may include multiple filars with each filar having a substantially uniformed composition throughout.

In some examples, rather than being a unitary core formed of the Ti alloys compositions described herein, lead wire 80 may include a Ta or Nb core wire with the core coated or otherwise surround by a Ti alloy composition material, e.g., where lead wire 80 includes a Ta or Nb core coated with a Ti-15Mo composition. Such a lead wire design may be employed to improve the resistance of the lead wire. For example, a lead wire made with smaller diameter (e.g., 0.003 inch) solid/unitary Ti15Mo wire may have relatively high resistance. The use of a cored wire design (e.g., with a Ta or Nb core) may reduce the resistance (resistivity) of such a lead wire. In some examples, lead wire 80 is a cored wire with a Ta or Nb core surrounded by a Ti-15Mo composition material. The core area fraction for lead wire 80 with a cored structure may be between about 20% to about 30% (e.g., for a cross-section orthogonal to the long axis of lead wire 80).

Lead wire 80 may be coated with an electrically insulative coating such as SI polyimide or other suitable coating. In the case of multiple electrodes, lead wires 80 and 83 may be individual filars of a coiled multi filar wire with each filar being coated and electrically coupled to a respective electrode and corresponding electrical contact. The insulative coating may electrically isolate the filars from each other within lead body 72 as well as the environment surrounding the multi-filar coiled wire.

As noted above, in some examples, it may be desirable for electrode substrate 80 to be formed of a composition other than that of Pt or alloys thereof, such, as, e.g., Pt—Ir, e.g., based on the weldability of Pt—Ir to Ti-15Mo lead wire. In accordance with some examples of the disclosure, electrode substrate 78 of electrode 74 may be formed of a beta titanium alloy to allow for conduction of electrical signals from lead wire 80 as well as allowing for substrate 78 to be welded, e.g., laser welded or resistance welded, to lead wire 80. For example, the titanium alloy used to form electrode substrate 78 may be a beta titanium alloy that includes at least about 90 volume percent (vol %) beta phase, such as, at least about 95 vol % beta phase. In one example, substrate 78 may consist essentially of Ti and one or more alloying elements that provides for the beta phase to be present in at least about 90 vol %, where any additional material is present only in an amount that does not alter one or more properties of the material in a manner that prevents substrate 78 from functioning as described herein.

Electrode substrate 78 may be a unitary structure formed of a substantially uniform beta Ti alloy composition such as that described herein. Example alloying elements for the beta Ti alloy may include one or more of Nb, Ta, Mo, V, W, Zr, Sn, and Hf. The specific alloying element(s) and amount thereof in the composition may influence one or more properties of the Ti alloy. In some examples, the specific alloying element(s) and amount thereof may be selected to provide for the desired beta phase content in the composition, the desired radiopacity, the desired weldability to lead wire 80, and/or other properties described herein. A beta-annealing process may be used when forming electrode substrate 80, e.g., to control one or more properties of substrate 80 such as grain size, microstructure, and/or the like.

In some examples, electrode substrate 80 may be formed of a TiTaSn alloy. Preferably, in some examples, the TiTaSn alloy may include about 46 wt % to about 54 wt % Ta and about 3.5 wt % to about 6.5 wt % Sn. The balance of the alloy may be titanium. In one example, the TiTaSn alloy may include about 48 wt % to about 52 wt % Ta and about 3 wt % to about 5 wt % Sn. The balance of the alloy may be titanium. In one example, electrode substrate 78 may be formed of a Ti50Ta4Sn alloy with about 50 wt % Ta, about 4 wt % Sn and the balance Ti. In one example, electrode substrate 78 may be formed of a Ti50Ta5Sn alloy with about 50 wt % Ta, about 5 wt % Sn and the balance Ti.

In some examples, the beta Ti alloy (e.g., TiTaSn alloy) employed for electrode substrate 78 may exhibit one or more desired properties. In some examples, the selected the beta Ti alloy (e.g., TiTaSn alloy) may have an ultimate tensile strength (UTS) of greater than about 110 kilopounds per square inch (ksi), an elongation at break of greater than about 12%, an elastic modulus of less than about 11000 ksi, an alpha phase amount of less than about 4 area percent or less than about 4 volume percent, and/or a grain size of less than 20 micrometers. The area percent of a particular phase may be a measurement taken from a cross-section of a sample, e.g., where the overall sample has the same or roughly the same volume percent.

In some examples, the beta titanium alloy may be selected such that electrode substrate 78 exhibits a radiopacity that is substantially the same or near that of a substrate formed of a Pt—Ir alloy. For example, in some instances, including Ta as an alloying element will improve the radiopacity of a beta titanium alloy. In some examples, the beta Ti alloy used to form electrode substrate 78 may include about 40 wt % of Ta in order to provide for the desired radiopacity of electrode substrate 78. Likewise, the content of Sn be about 3 wt %.

While the use of one or more of alloys describe above to form substrate 78 may provide for one or more benefits, in some examples, beta Ti alloys may have a relatively low charge density limits compared to that of Pt based alloys, which may decrease the effectiveness for delivering electrical stimulation current. In accordance with one of aspects of this disclosure, coating 76 may be applied to outer surface of electrode substrate 78. The coating of composition may increase the charge density of electrode 74 by increasing the surface roughness along with providing a fractal morphology that results in a large increase in effective surface area compared to that of the surface of electrode substrate 78. Also, the combination of electrode substrate 78 and coating 76 may provide for a reduced electrode impedance compared to that of Pt-10Ir electrodes. In some cases, lower overall impedance will reduce energy consumption and increase device life.

Coating 76 on substrate 78 may be formed of a composition comprising at least one of Pt (fractal Pt), graphene (fractal graphene), TiN, IrOx, or PEDOT. For examples utilizing Pt coatings, the composition of coating 76 may be substantially all Pt or alloyed with one or more elements, such as, e.g., Jr, Rh, and Au. For examples utilizing TiN coatings, the composition of coating 76 may include any suitable ratio of Ti to N, e.g., a ratio of approximately 1:1. Coating 76 may have a composition that provides for a relatively large increase in the effective surface roughness and effective surface area compared to that of the uncoated electrode substrate surface. In one example, coating 76 may consist essentially of one or more of Pt (fractal Pt), graphene (fractal graphene), TiN, IrOx, and PEDOT, where any additionally material is present only in an amount that does not alter one or more properties of the material in a manner that does not allow coating 76 to function as described herein.

Surface coating 76 may be deposited on the outer surface of substrate 78 to define any suitable thickness over substrate. For example, coating 76 may have a thickness between approximately 0.5 micrometers and approximately 15 micrometers or less than about 3 micrometers. Coating 76 may have a substantially uniform thickness over the surface of substrate 78 or, alternatively, may vary in thickness. In some examples, coating 76 may cover substantially the entire exposed outer surface of substrate 78.

Any suitable technique may be used to form coating 76 on substrate 78. For example, coating 76 may be deposited using sputtering, such as, e.g., vacuum sputtering, PVD, CVD, or plasma enhanced deposition process when the composition of coating 76 includes one or more of Pt, TiN, or IrOx. As another example, when coating 76 is formed of conductive PEDOT, electropolymerization techniques may be used.

In some examples (e.g., as an alternative to coating 76), outer surface of substrate 78 may be modified by laser beam to create microscopic/nanoscopic features to increase effective surface area of the outer surface. The increase in effective surface area may increase charge injection capacity.

Lead wire 80 may be attached to electrode substrate 78 by welding such as laser welding or resistance welding. A single weld or multiple welds at different locations may be used to connect lead wire 80 to substrate 78.

While FIGS. 5A and 5B only show electrode 74 and lead wire 80, the description of electrode 74 and lead wire 80 may also apply to electrode 69 and lead wire 72 shown in FIG. 4. The composition of the electrode substrate for electrode 69 may be the same or different than that of electrode 74. The composition of lead wire 83 may be the same or different than that of lead wire 80.

Figure 6A:
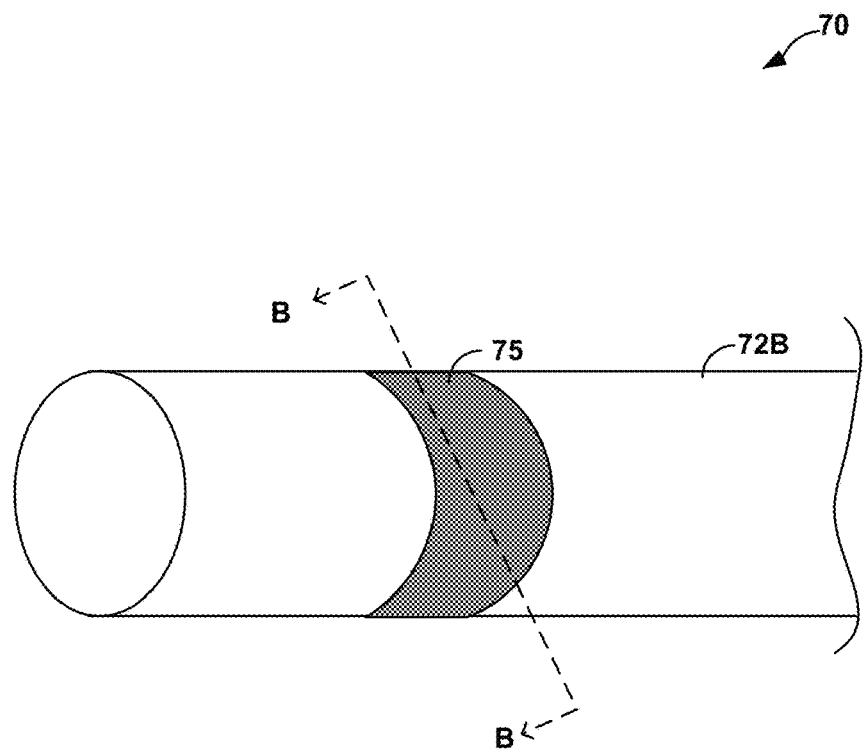
FIG. 6A is a conceptual diagram illustrating the proximal portion an example medical device lead including an electrical contact.
Figure 6B:
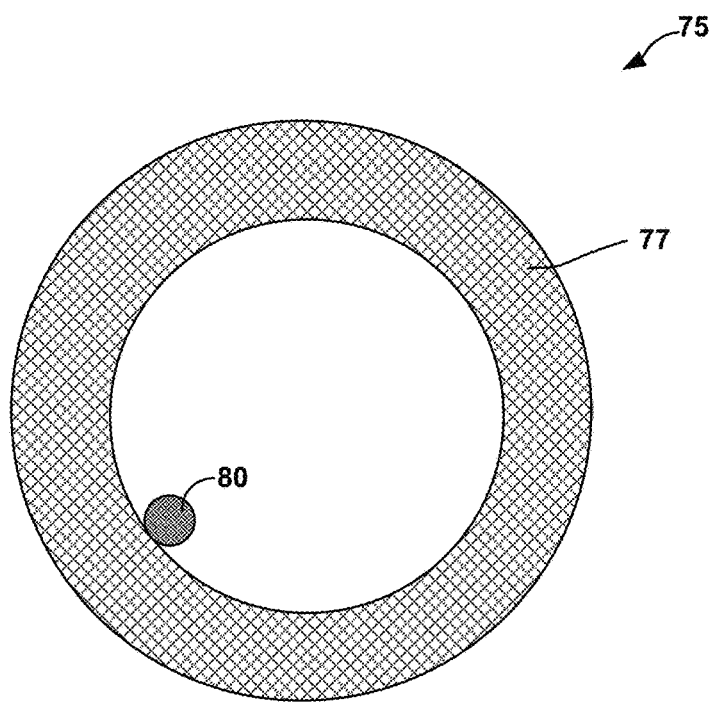
FIG. 6B is a conceptual diagram illustrating the example medical device lead of FIG. 6A along cross-section B-B.

FIG. 6A is a conceptual diagram illustrating a part of proximal portion 72B of lead 70 shown in FIG. 4. FIG. 6B is a conceptual diagram illustrating the example medical device lead of FIG. 6A along cross-section B-B. As shown, electrical contact 75 includes contact substrate 77. The outer surface of contact substrate 77 may interface with an opposing contact in a lead extension or header of an IMD to electrically connect contact substrate 77 to circuitry of the IMD, such as sensing module 46 and/or stimulation generator 44 of IMD 16. The inner surface of substrate 77 is mechanically and electrically coupled to conductive lead wire 80. Electrical stimulation may be delivered to patient 12 via electrode 74 by conducting electrical stimulation current generated by IMD 16 from lead wire 80 to electrode substrate 78 via contact substrate 77. Likewise, for sensing with electrode 74, electrical signals may be transmitted across contact substrate 77 from lead wire 80 and electrode substrate 78 to IMD 16. Lead wire 80 may be attached to contact substrate 77 by welding such as laser welding or resistance welding. A single weld or multiple welds at different locations may be used to connect lead wire 80 to contact substrate 77.

Contact substrate 77 may be formed of a beta Ti alloy, which may be the same or different from that of the beta Ti alloy used to form electrode substrate 78 or lead wire 80. Example alloying elements for the beta Ti alloy may include one or more of Nb, Ta, Mo, V, W, Zr, Sn, and Hf. The specific alloying element(s) and amount thereof in the composition may influence one or more properties of the beta Ti alloy. In some examples, the beta titanium alloy used to form contact substrate 77 may be a titanium alloy that includes as least about 90 vol % beta phase, such as, at least about 95 vol % beta phase or about 96 vol % beta phase. In some examples, the grain size of the beta titanium alloy composition may be about 20 micrometers or less. A beta-annealing process may be used when forming contact substrate 77, e.g., to control one or more properties of substrate 77 such as grain size, microstructure, and/or the like.

In some examples, substrate 77 is formed of a Ti alloy alloyed with Mo such as Ti-15Mo (e.g., a Ti-based alloy with about 15 wt % Mo). In one example, substrate 77 is formed of a Ti—Mo alloy, e.g., wherein Mo is present in between about 5 wt % to about 25 wt %. In some examples, the Ti—Mo alloy may include one or more additional alloying elements or may only include Ti—Mo in the alloy composition (e.g., about 5 wt % to about 25 wt % Mo with a remainder being Ti). In some examples, the Ti-15Mo alloy may include one or more additional alloying elements such as Zr and/or Al (e.g., as a Ti15Mo5Zr3Al alloy with about 15 wt % Mo, about 5 wt % Zr about 3 wt % Al with the remainder being Ti). In some examples, the beta Ti alloy may be beta 21S (Ti15Mo3Al3Nb0.5Si). The particular alloy composition may be selected such that contact substrate 77 is weldable to lead wire 80 (such as a Ti-15Mo lead wire) and/or exhibits one or more desired properties, such as being formable as a rod, tube, and/or strip.

In one example, substrate 77 may consist essentially of a titanium alloyed with one or more elements, where any additionally material is present only in an amount that does not alter one or more properties of the material in a manner that prevents lead 70 from functioning as described herein.

In the example shown in FIGS. 6A and 6B, contact substrate 77 is in the form of a tubular ring. For example, contact substrate 77 may be machined from beta annealed Ti-15Mo rod or tube to form a ring shape. Other shapes for the contact substrate 77 are contemplated. While FIGS. 6A and 6B only show contact 75 and lead wire 80, the description of contact 75 and lead wire 80 may also apply to contact 67 and lead wire 83 shown in FIG. 4. The composition of the contact substrate for contact 67 may be the same or different than that of contact 75. The composition of lead wire 83 may be the same or different than that of lead wire 80.

Figure 7A:
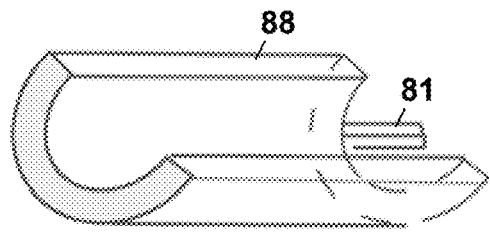
FIGS. 7A-7D are conceptual diagrams illustrating example electrode, electrical contact, and lead wire shapes.
Figure 7B:
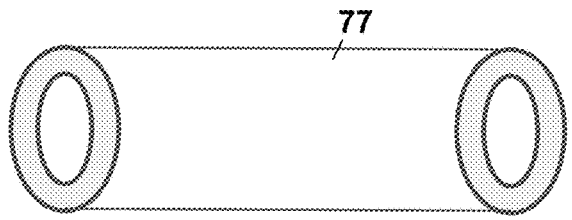

FIGS. 7A and 7B are conceptual diagrams showing example shape for an electrode substrate and a contact substrate, respectively, such as for electrode 78 and contact 75. FIG. 7A shows a half or partial tube substrate 88 with a tab 81 for welding to lead wire 80. FIG. 7B shows a ring or tube shaped substrate 87 that may define a single ring electrode. The shape of electrode substrate 78 and contact substrate 77 may be varied depending on the desired application. In some examples, electrode substrate 78 may be a tube or ring like that shown in FIGS. 5A and 5B, or a paddle with a substantially planar surface and a tab. A half tube substrate such as that shown in FIG. 7A may be used to define a single electrode, e.g., at a distal portion of a lead for peripheral nerve stimulation.

Figure 7C:
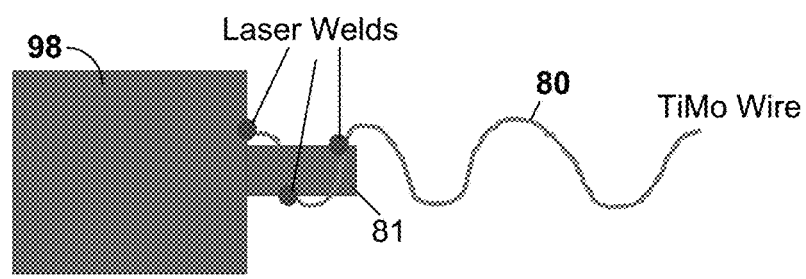
Figure 7D:
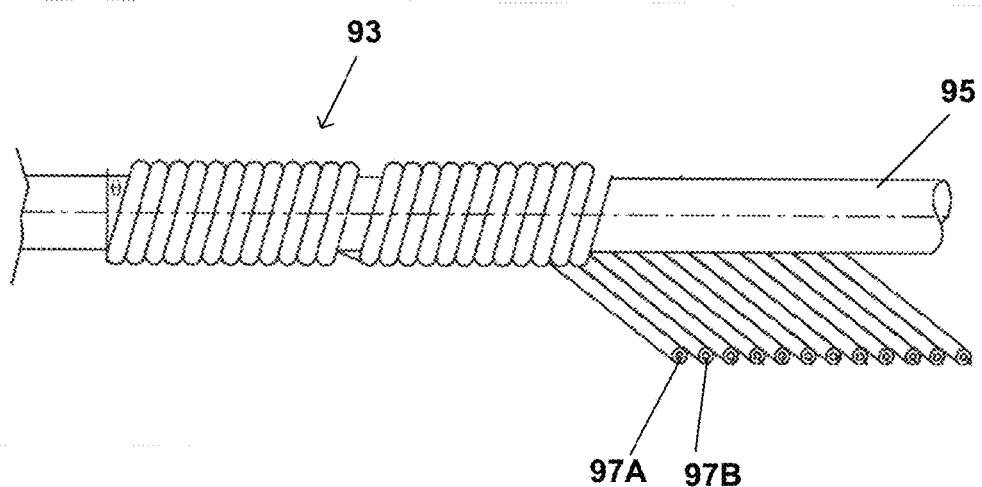

FIG. 7C is a conceptual diagram illustrating another example electrode substrate 98 with a paddle shape and tab 81. Substrate 98 may define, e.g., a single electrode or multiple electrodes such as 4 to 8 electrodes. As shown in FIG. 7C, a coiled lead wire 80 may be welded to tab 81 at one or more locations. Although not shown, the opposite end of coiled lead wire 80 may be welded to electrical contact substrate 77.

FIG. 7D is a conceptual diagram illustrating a portion of multi-filar coiled lead wire 93. Lead wire 93 includes twelve filars (e.g., filars 97A and 97B) coiled around mandrels 95, which may be used during the coiling process to form lead wire 93. Each filar may be formed of a titanium or titanium alloy composition described herein for example lead wires. Each individual filar may be coated with an electrical insulator to electrically isolate the respective filars from each other in the coiled structure. In some examples, a coiled lead wire 93 may include a beta titanium alloy such as Ti-15Mo that is cold drawn and coated with an electrical insulator such as SI polyimide and formed into a coil with multiple filars, e.g., with coiled lead wire 93 include about four to twelve filars.

In some examples, a tube substrate such as that shown in FIG. 7B used for an electrode substrate or contact substrate may have outer diameter of approximately 4.25 millimeters and an inner diameter of approximately 4 millimeters. In the case of a cylindrical rod substrate, the rod may have a diameter of less than about 5 millimeters. To form a ring electrode, the rod substrate may be machined to form a ring shaped substrate such as that shown in FIG. 7B. In some examples, the paddle shown in FIG. 7C may have a thickness of about 0.003 inches to about 0.006 inches. In some examples, a paddle lead may be about 0.015 inches to about 0.055 inches thick, about 0.10 to about 0.4 inches in width, and about 0.3 inches to about 1 inch in length. Other shapes and dimensions are contemplated.

One or more heat treatments may be employed when forming the electrode substrates, contact substrates, and lead wire. In some examples, the heat treatment may be in the form of a beta annealing process, e.g., for a ring shaped electrode substrate. In some examples, the heat treatment may be a stress relieving heat treatment, e.g., for a paddle shaped electrode substrate.

Electrode substrate 78 and contact substrate 77 may be formed using any suitable technique. As noted above, the particular beta-Ti alloy compositions selected for substrate 78 and substrate 77 may beneficially provide for a high degree of formability when manufacturing substrate 78 and substrate 77. In some examples, a material formed of the beta-titanium alloy composition used for substrate 78 or substrate 77 may be drawn into a tube. In the case of electrode substrate 78, the tube may then be machined (e.g., laser machined) and/or cut (e.g., laser cut) as needed to form the desired substrate shape. In another example, a rod may be formed of the desired beta-Ti alloy material and then machined (e.g., laser machined) and/or cut (e.g., laser cut) as needed to form the desired substrate shape.

Although examples of the present disclosure have primarily been described with regard to ring electrodes, examples are not limited as such. For example, in some cases a lead may include one or more segmented electrodes. The segments electrodes may each include an electrode substrate coupled (e.g., welded) to a lead wire having those compositions described herein. The outer surface of the electrode substrate for each of the segmented electrodes may be coated with those compositions described herein or may be uncoated. Each segment of a segmented electrode may be coupled to a separate lead wire and separate contact to allow for electrical signals to be independently delivered by each segment.

As another example, examples of the disclosure may include paddle leads having any suitable shape and configuration, e.g., a paddle lead with a two dimensional array of electrodes on the surface of the paddle electrodes. In some examples, each electrode located on the paddle lead may include an electrode substrate coupled (e.g., welded) to a lead wire having those compositions described herein. The outer surface of the electrode substrate for each of the electrodes on a paddle lead may be coated with those compositions described herein or may be uncoated.

Figure 8:
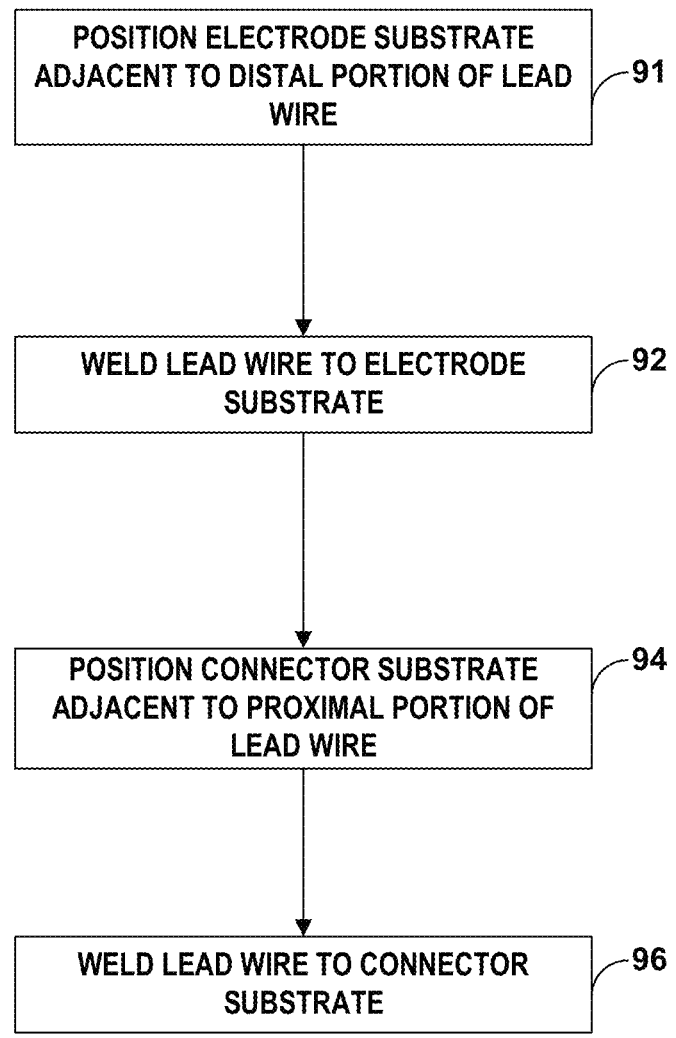
FIG. 8 is a flow diagram illustrating an example technique for assembling a medical lead including an electrode, lead wire, and contact.

The components of the example medical leads described may be assembled in any suitable manner. FIG. 8 is a flow diagram illustrating an example technique for attached an electrode substrate and contact substrate to a coiled lead wire. For ease of description, the example of FIG. 8 will be described with reference to electrode 74, contact 75, and lead wire 80 of lead 70 described above. As shown, electrode substrate 78 may be positioned adjacent to a distal portion of lead wire 80 (91). Lead wire 80 may be a coiled, multi filar wire in some examples. When electrode substrate 78 is positioned adjacent to the desired portion of lead wire 80, lead wire 80 may be welded to the opposing portion of electrode substrate 78 (92). The welding process may be a laser welding process in which a concentrated energy source (e.g., as laser) heats the lead wire 80 and/or electrode substrate 78 to melt opposing portions of lead wire 80 and/or electrode substrate 78, followed by cooling/solidification of the materials to form a weld. The welding process may also be a resistance welding process in which an electrical current is passed through lead wire 80 and substrate 78 to melt the materials via electrical resistance heating, followed by cooling/solidification to form a weld. Other suitable welding technique may be used besides laser welding and resistance welding. In some examples, techniques other than welding may also be used to attach substrate 78 to wire 80.

A similar process may then be used in which contact substrate 77 is positioned adjacent to a proximal portion of lead wire 80 (94) and then substrate 77 is welded to the opposing portion of lead wire 80 (96), e.g., using one or more of the techniques described above for attaching lead wire 80 to electrode substrate 78. This process may be performed for multiple electrodes, lead wires, and contacts as needed.

The sequence of steps shown in FIG. 8 are only for descriptive purposes, and in some examples, electrode substrate 78 may be welded to lead wire 80 after or at the same time as contact substrate 77. Further processing may be carried out on lead wire 80, electrode substrate 78 and contact substrate 77 to form a medical lead, such as lead 20A or lead 20B. For example, an outer insulative material layer may be formed of an electrically insulative material such as aromatic polyether urethane 55D, 75D, 80A, aromatic or aliphatic polycarbonate urethane 95A, 55D, 65D, 75D, silicone rubber to enclose lead wire 80 within lead body 72, e.g., by an overmolding process, with a portion of electrode 74 and contact 75 being exposed, e.g., through a window in the insulative coating, to allow for the conduction of electrical current as described herein.

Examples

As series of experiments were performed to evaluate one or more aspects related to the present disclosure.

A study was carried out that indicated that Ti and Pt are not weldable to each other to a level that was desired for the intended application. In the study, laser welds were attempted between a Ti-based lead wire and a PtIr electrode substrate for a variety of samples using multiple laser welding parameters. Evaluation of the laser welds in the samples showed the formation of multiple brittle phases and the welds were found to crack after welding. The break load of the Ti lead wire and PtIr electrode substrate weld had wide distribution ranging from approximately zero pounds (lbs) to one lb.

It was determined based in part on the study that an alloy weldable to Ti-15Mo wire was desirable. In some cases, the wire drawing process for forming a Ti alloy lead wire such as a Ti-15Mo lead wire caused high H content (e.g., greater than 300 ppm) in the Ti-15Mo wire. As such, it was believed that an alpha Ti alloy will not be able to be used for the electrode substrate. After testing, it was determined that Ti alloys, such as those beta Ti alloys described herein, could meet the desired laser welding requirements.

Figure 9:
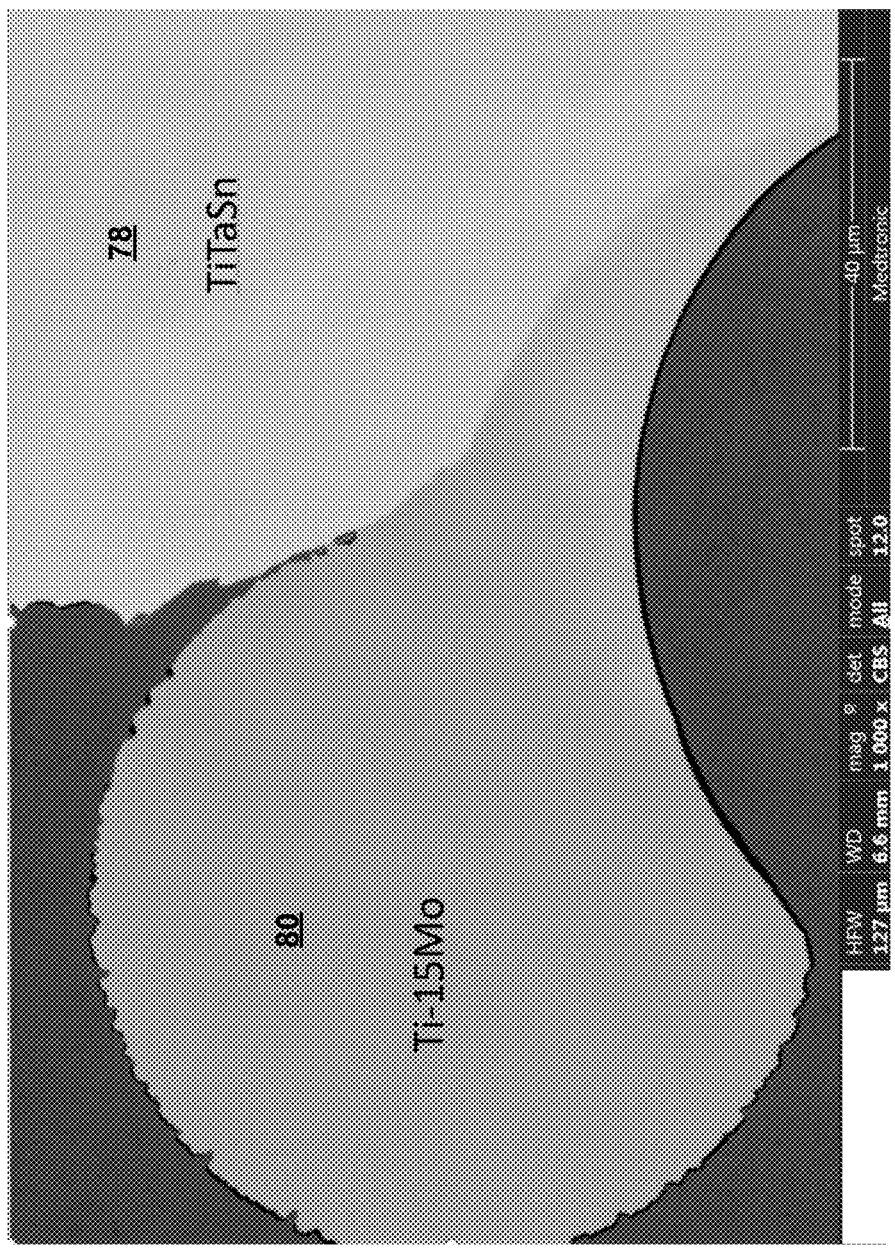
FIGS. 9-12 are various images related to experimental tests carried out to evaluate aspects of the disclosure.

FIG. 9 is a scanning electron microscope (SEM) image showing a laser weld between a Ti-15Mo (85 wt % Ti and 15 wt % Mo) lead wire 80 and a Ti50Ta4Sn electrode substrate 78. The composition of the Ti-15Mo wire 80 included beta phase and the composition of the TiTaSn electrode substrate 78 also included beta phase. An evaluation of the sample shown in FIG. 9 indicated that a suitable weld was formed between the materials.

Figure 10:
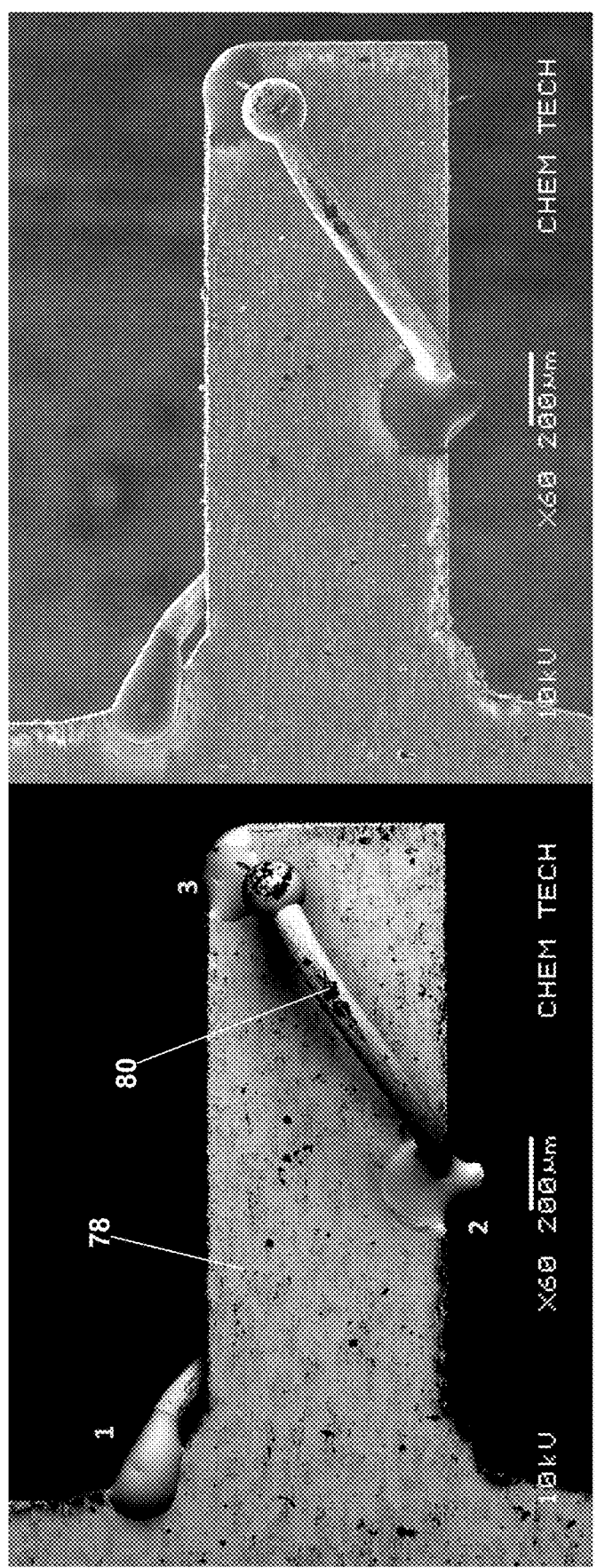

FIG. 10 is a pair of backscattered electron and secondary electron images showing a laser weld between an example Ti50Ta4Sn paddle electrode substrate 78 and a Ti-15Mo coiled lead wire 80. Ti-15Mo coiled lead wire was laser welded on the beta Ti alloy paddle electrode substrate 78 at locations 1, 2, and 3. The welds between the wire and electrode substrate were determined to be satisfactory.

Figure 11:
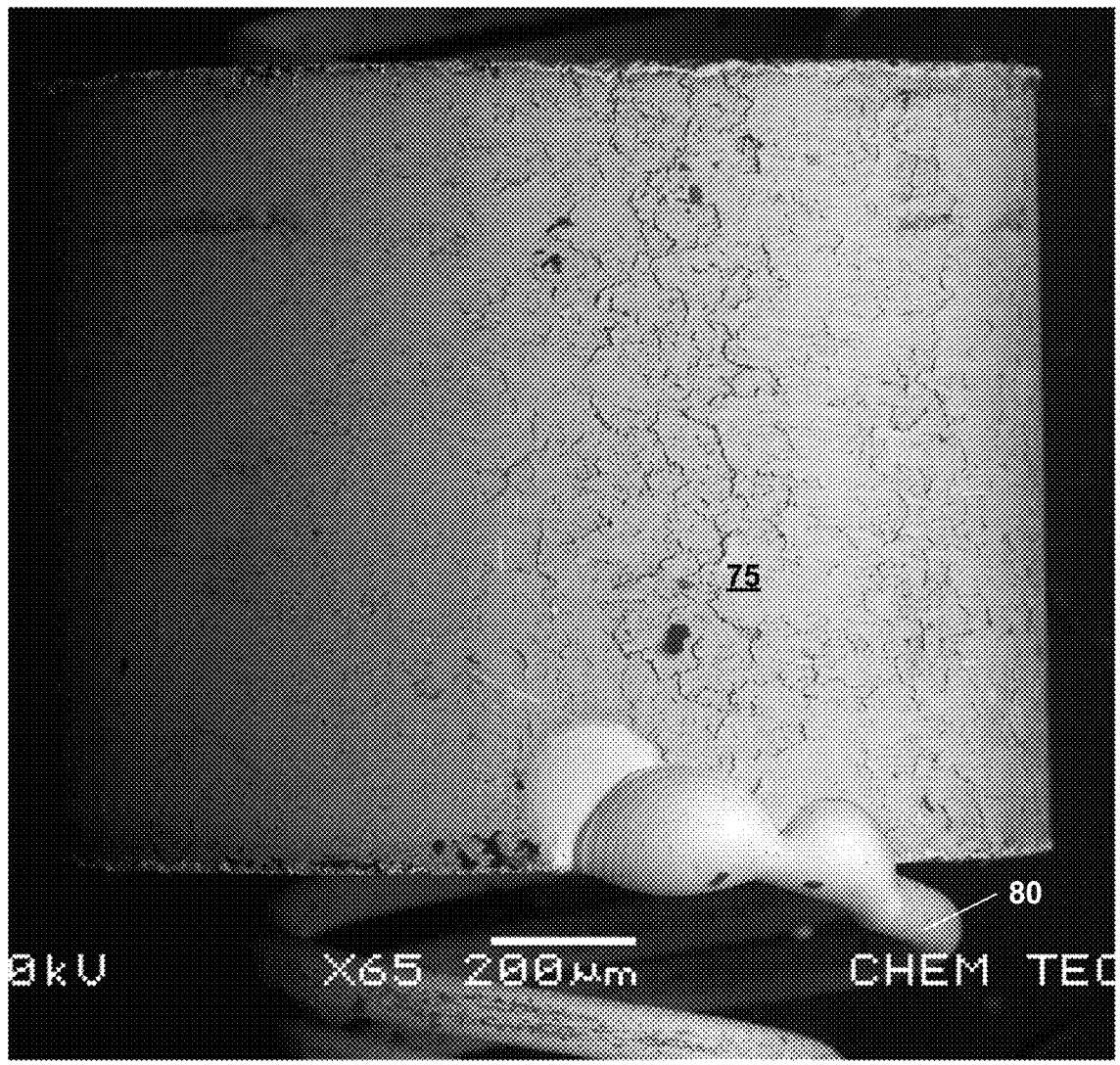

FIG. 11 is an image showing a laser weld formed between a Ti-15Mo lead wire 80 and an electrical contact substrate 75 in the form of a Ti15Mo5Zr3Al ring.

In addition to the weldability of various materials, the radiopacity of various materials was also investigated. Since it was determined that a Pt—Ir alloy was not weldable to Ti-15Mo wire to the desired degree, several Ti alloys were evaluated to compare radiopacity to Pt—Ir alloy electrode. Four beta Ti alloys were evaluated (i.e., Ti15Mo5Zr3Al, Ti45Nb, Ti29Nb10Ta5Zr and Ti50Ta4Sn) for their radiopacity.

Figure 12:
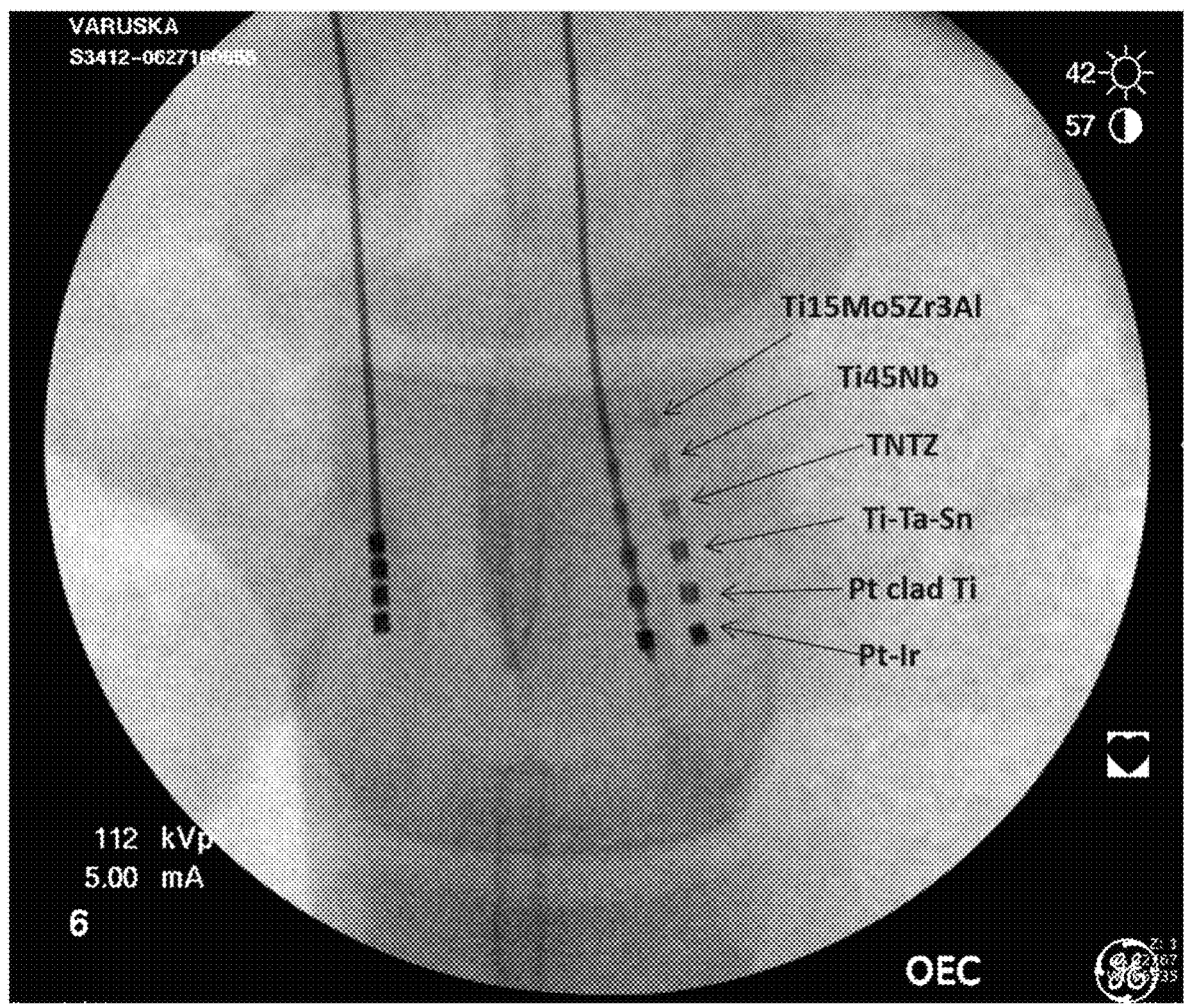

FIG. 12 is a fluoroscopic X-ray image showing ring electrodes substrates on a medical lead with the four beta Ti alloys plus a Pt—Ir alloy. As shown, the radiopacity of the alloy depends on alloy composition. The Pt—Ir electrode substrate had the darkest contrast and the Ti15Mo3Al had the lowest contrast. Ti50Ta4Sn electrode substrate had a contrast substantially similar/comparable to the Pt—Ir electrode and was considered as acceptable contrast. Thus, it was considered that the TiTaSn alloy had comparable radiopacity to the Pt—Ir alloy.

In view of the above studies, it was determined that a TiTaSn (Ti50Ta4Sn) alloy electrode substrate was able to meet laser welding and radiopacity requirement.

Figure 13:
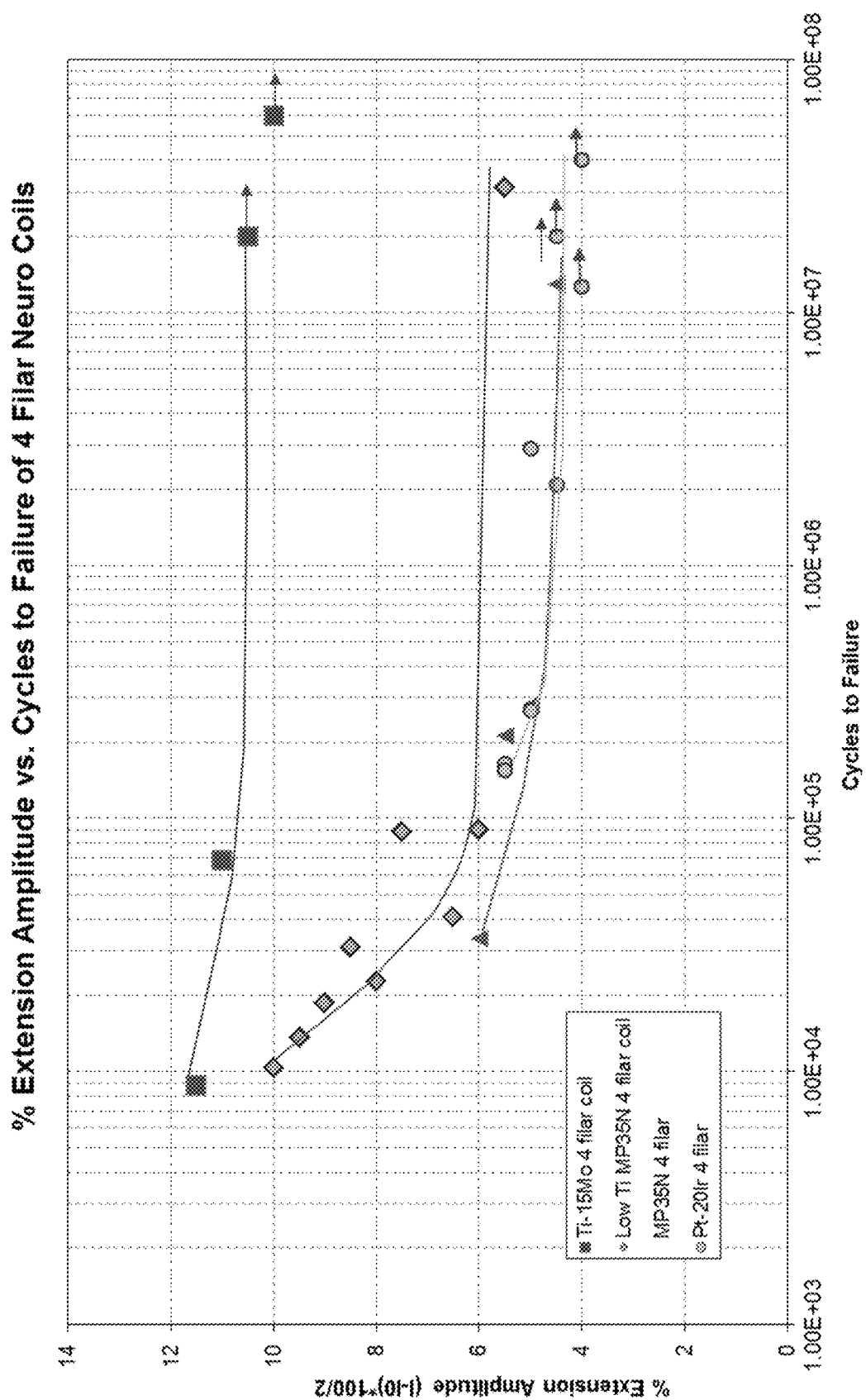
FIG. 13 is a plot of extension amplitude versus cycles to failure for a lead wire in accordance with an example of the disclosure.

The fatigue endurance of a Ti-15Mo coiled lead wire was also evaluated. FIG. 13 is a plot showing the fatigue S-N curve for coiled lead wires with different compositions. The four coils were made of MP35N, LT-MP35N, Pt20Ir and Ti-15Mo wires. The Y-axis in FIG. 13 is the amplitude of displacement on the coil in coil length direction. Each coil had an outer diameter of approximately 0.027 inches. The plot shows that Ti-15Mo coil had a fatigue endurance limit approximately twice that of the MP35N coil.

In one instance, it was determined that a SI coated Ti-15Mo wire had a fatigue endurance at 1.1% and MP35N wire had a fatigue endurance limit at 0.45%.

Various examples of the disclosure have been described. These and other examples are within the scope of the following clauses and claims.

Clause 1. A medical lead comprising: a lead body including an electrically conductive lead wire; an electrical contact on a proximal portion of the lead body, the electrical contact comprising a contact substrate; and an electrode on a distal portion of the lead body, the electrode comprising an electrode substrate, wherein the electrode substrate is electrically coupled to the contact substrate via the electrically conductive lead wire, wherein the lead wire is formed of a composition comprising titanium or titanium alloys, wherein the electrode substrate is formed of a first beta-titanium alloy, and wherein the contact substrate is formed of a second beta-titanium alloy.

Clause 2. The medical lead of clause 1, wherein the first beta-titanium alloy comprises a TiTaSn alloy.

Clause 3. The medical lead of clause 2, wherein the TiTaSn alloy includes about 46 wt % to about 54 wt % Ta and about 3.5 wt % to about 6.5 wt % Sn.

Clause 4. The medical lead of clause 3, wherein a balance of the TiTaSn alloy is titanium.

Clause 5. The medical lead of any one of clauses 1-4, wherein the first beta-titanium alloy exhibits a radiopacity similar to that of a Pt—Ir alloy.

Clause 6. The medical lead of any one of clauses 1-5, wherein the second beta alloy comprises a Ti-15Mo alloy.

Clause 7. The medical lead of clause 6, wherein the Ti-15Mo alloy comprises a Ti15Mo5Zr3Al alloy.

Clause 8. The medical lead of any one of clauses 1-7, wherein the electrode substrate and the contact substrate are each attached to the lead wire by at least one of laser welding or resistance welding.

Clause 9. The medical lead of any one of clauses 1-8, further comprising a coating or a laser modified surface layer on an outer surface of the electrode substrate.

Clause 10. The medical lead of clause 9, wherein the coating comprises at least one of Pt, TiN, IrOx, and poly(3, 4-ethylenedioxythiophene) (PEDOT).

Clause 11. The medical lead of any one of clauses 1-10, wherein the composition of the lead wire comprises a Ti15Mo alloy.

Clause 12. The medical lead of any one of clauses 1-11, wherein the lead wire is in a coiled form within the lead body.

Clause 13. The medical lead of any one of clauses 1-12, wherein the lead wire is coated with an electrical insulator.

Clause 14. The medical lead of any one of clauses 1-13, wherein the electrical insulator comprises an SI polyimide.

Clause 15. The medical lead of any one of clause 1-14, wherein the electrode is one of a ring electrode or a segmented electrode.

Clause 16. The medical lead of any one of clause 1-15, wherein the lead wire, the electrode substrate, and the contact substrate are formed of different compositions.

Clause 17. The medical lead of any one of clause 1-16, wherein the first beta titanium alloy and the second beta titanium alloy are different alloys.

Clause 18. The medical lead of any one of clauses 1-16, wherein the first beta titanium alloy and the second beta titanium alloy are the same alloys.

Clause 19. The medical lead of any one of clauses 1-18, wherein the electrode comprises a first electrode, the electrical contact comprises a first electrical contact, and the lead wire comprises a first lead wire, the medical lead further comprising a second electrode on the distal portion of the lead body, a second electrical contact on the proximal portion of the lead body, and a second lead wire, and wherein a second electrode substrate of the second electrode is electrically coupled to a second contact substrate of the second contact via the second lead wire.

Clause 20. The medical lead of clause 19, wherein the second electrode is positioned at a different axial position of the lead body than the first electrode.

Clause 21. The medical lead of clause 19, wherein the second electrode substrate is formed of the first beta-titanium alloy and the second contact substrate is formed of the second beta-titanium alloy.

Clause 22. The medical lead of any one of clauses 1-21, wherein the first beta Ti alloy has at least one of an ultimate tensile strength (UTS) of greater than about 110 kilopounds per square inch (ksi), an elongation of greater than about 12%, an elastic modulus of less than about 11000 ksi, an alpha phase volume fraction of less than about 4 percent, or a grain size of less than 20 micrometers.

Clause 23. The medical lead of any one of clauses 1-22, wherein the lead wire is formed of a third beta titanium alloy.

Clause 24. The medical lead of clause 23, wherein the third beta titanium alloy is different that at least one of the first beta titanium alloy or the second beta titanium alloy.

Clause 25. A medical device comprising: the medical lead of any one of clauses 1-24; and a medical device including an electrical stimulation generator, wherein the lead is configured to be electrically coupled to the stimulation generator such that electrical stimulation signals may be transmitted from the electrical stimulation generator to the electrode substrate via the lead wire and the contact substrate.

Clause 26. A method for assembling a medical lead, the assembled medical lead comprising: a lead body including an electrically conductive lead wire; an electrical contact on a proximal portion of the lead body, the electrical contact comprising a contact substrate; and an electrode on a distal portion of the lead body, the electrode comprising an electrode substrate, the method comprising: attaching the lead wire to the electrode substrate; and attaching the lead wire to the contact substrate to electrically couple the electrode substrate to the contact substrate via the electrically conductive lead wire, wherein the lead wire is formed of a composition comprising titanium or titanium alloys, wherein the electrode substrate is formed of a first beta-titanium alloy, and wherein the contact substrate is formed of a second beta-titanium alloy.

Clause 27. The method of clause 26, wherein attaching the lead wire to the electrode substrate comprises welding the electrode substrate to a distal portion of the lead wire, and wherein attaching the lead wire to the contact substrate comprises welding the contact substrate to a proximal portion of the lead wire.

Clause 28. The method of clause 27, wherein welding the electrode substrate to the distal portion comprises at least one of laser welding or resistance welding.

Clause 29. The method of any one of clauses 26-28, wherein the first beta-titanium alloy comprises a TiTaSn alloy.

Clause 30. The method of clause 29, wherein the TiTaSn alloy includes about 46 wt % to about 54 wt % Ta and about 3.5 wt % to about 6.5 wt % Sn.

Clause 31. The method of clause 30, wherein a balance of the TiTaSn alloy is titanium.

Clause 32. The method of any one of clauses 26-31, wherein the first beta-titanium alloy exhibits a radiopacity similar to that of a Pt—Ir alloy.

Clause 33. The method of any one of clauses 26-32, wherein the second beta alloy comprises a Ti-15Mo alloy.

Clause 34. The method of clause 33, wherein the Ti-15Mo alloy comprises a Ti15Mo5Zr3Al alloy.

Clause 35. The method of any one of clauses 26-34, further comprising forming a coating or a laser modified surface layer on an outer surface of the electrode substrate.

Clause 36. The method of clause 35, wherein the coating comprises at least one of Pt, TiN, IrOx, and poly(3,4-ethylenedioxythiophene) (PEDOT).

Clause 37. The method of any one of clauses 26-36, wherein the composition of the lead wire comprises a Ti15Mo alloy.

Clause 38. The method of any one of clauses 26-37, wherein the lead wire is in a coiled form within the lead body.

Clause 39. The method of any one of clauses 26-38, wherein the lead wire is coated with an electrical insulator.

Clause 40. The method of any one of clauses 26-39, wherein the electrical insulator comprises an SI polyimide.

Clause 41. The method of any one of clause 26-40, wherein the electrode is one of a ring electrode or a segmented electrode.

Clause 42. The method of any one of clause 26-41, wherein the lead wire, the electrode substrate, and the contact substrate are formed of different compositions.

Clause 43. The method of any one of clause 26-42, wherein the first beta titanium alloy and the second beta titanium alloy are different alloys.

Clause 44. The method of any one of clauses 26-42, wherein the first beta titanium alloy and the second beta titanium alloy are the same alloys.

Clause 45. The method of any one of clauses 26-44, wherein the electrode comprises a first electrode, the electrical contact comprises a first electrical contact, and the lead wire comprises a first lead wire, the medical lead further comprising a second electrode on the distal portion of the lead body, a second electrical contact on the proximal portion of the lead body, and a second lead wire, and wherein a second electrode substrate of the second electrode is electrically coupled to a second contact substrate of the second contact via the second lead wire.

Clause 46. The method of clause 45, wherein the second electrode is positioned at a different axial position of the lead body than the first electrode.

Clause 47. The method of clause 45, wherein the second electrode substrate is formed of the first beta-titanium alloy and the second contact substrate is formed of the second beta-titanium alloy.

Clause 48. The method of any one of clauses 26-47, wherein the first beta Ti alloy has at least one of an ultimate tensile strength (UTS) of greater than about 110 kilopounds per square inch (ksi), an elongation of greater than about 12%, an elastic modulus of less than about 11000 ksi, an alpha phase volume fraction of less than about 4 percent, or a grain size of less than 20 micrometers.

Clause 49. The method of any one of clauses 26-48, wherein the lead wire is formed of a third beta titanium alloy.

Clause 50. The method of clause 49, wherein the third beta titanium alloy is different that at least one of the first beta titanium alloy or the second beta titanium alloy.

The invention claimed is:

1. A medical lead comprising:
a lead body including an electrically conductive lead wire;
an electrical contact on a proximal portion of the lead body, the electrical contact comprising a contact substrate; and
an electrode on a distal portion of the lead body, the electrode comprising an electrode substrate,
wherein the electrode substrate is electrically coupled to the contact substrate via the electrically conductive lead wire,
wherein the lead wire is formed of a composition comprising titanium or titanium alloys,
wherein the electrode substrate is formed of a first beta-titanium alloy, wherein the first beta-titanium alloy comprises a TiTaSn alloy, and
wherein the contact substrate is formed of a second beta-titanium alloy.

2. The medical lead of claim 1, wherein the TiTaSn alloy includes about 46 wt % to about 54 wt % Ta and about 3.5 wt % to about 6.5 wt % Sn.

3. The medical lead of claim 2, wherein a balance of the TiTaSn alloy is titanium.

4. The medical lead of claim 1, wherein the electrode substrate and the contact substrate are each attached to the lead wire by at least one of laser welding or resistance welding.

5. The medical lead of claim 1, further comprising a coating or a laser modified surface layer on an outer surface of the electrode substrate.

6. The medical lead of claim 1, wherein the lead wire is coated with an electrical insulator, wherein the electrical insulator comprises an SI polyimide.

7. The medical lead of claim 1, wherein the lead wire, the electrode substrate, and the contact substrate are formed of different compositions.

8. The medical lead of claim 1, wherein the first beta titanium alloy and the second beta titanium alloy are different alloys.

9. The medical lead of claim 1, wherein the first beta titanium alloy and the second beta titanium alloy are the same alloys.

10. The medical lead of claim 1, wherein the electrode comprises a first electrode, the electrical contact comprises a first electrical contact, and the lead wire comprises a first lead wire, the medical lead further comprising a second electrode on the distal portion of the lead body, a second electrical contact on the proximal portion of the lead body, and a second lead wire, and wherein a second electrode substrate of the second electrode is electrically coupled to a second contact substrate of the second contact via the second lead wire, wherein the second electrode is positioned at a different axial position of the lead body than the first electrode, and wherein the second electrode substrate is formed of the first beta-titanium alloy and the second contact substrate is formed of the second beta-titanium alloy.

11. The medical lead of claim 1, wherein the lead wire is formed of a third beta titanium alloy.

12. The medical lead of claim 11, wherein the third beta titanium alloy is different than at least one of the first beta titanium alloy or the second beta titanium alloy.

13. A medical device comprising a medical lead, the medical lead comprising:
a lead body including an electrically conductive lead wire;
an electrical contact on a proximal portion of the lead body, the electrical contact comprising a contact substrate; and
an electrode on a distal portion of the lead body, the electrode comprising an electrode substrate,
wherein the electrode substrate is electrically coupled to the contact substrate via the electrically conductive lead wire,
wherein the lead wire is formed of a composition comprising titanium or titanium alloys,
wherein the electrode substrate is formed of a first beta-titanium alloy, wherein the contact substrate is formed of a second beta-titanium alloy, and
wherein the second beta alloy comprises a Ti-15Mo alloy.

14. The medical device of claim 13, wherein the Ti-15Mo alloy comprises a Ti15Mo5Zr3Al alloy.

15. The medical device of claim 13, further comprising a medical device including an electrical stimulation generator, wherein the medical lead is configured to be electrically coupled to the stimulation generator such that electrical stimulation signals may be transmitted from the electrical stimulation generator to the electrode substrate via the lead wire and the contact substrate.

16. A medical device comprising a medical lead, the medical lead comprising:
a lead body including an electrically conductive lead wire;
an electrical contact on a proximal portion of the lead body, the electrical contact comprising a contact substrate; and
an electrode on a distal portion of the lead body, the electrode comprising an electrode substrate,
wherein the electrode substrate is electrically coupled to the contact substrate via the electrically conductive lead wire,
wherein the lead wire is formed of a composition comprising titanium or titanium alloys,
wherein the electrode substrate is formed of a first beta-titanium alloy,
wherein the contact substrate is formed of a second beta-titanium alloy, and
wherein the first beta Ti alloy has at least one of an ultimate tensile strength (UTS) of greater than about 110 kilopounds per square inch (ksi), an elongation of greater than about 12%, an elastic modulus of less than about 11000 ksi, an alpha phase volume fraction of less than about 4 percent, or a grain size of less than 20 micrometers.

17. The medical device of claim 16, further comprising a medical device including an electrical stimulation generator, wherein the medical lead is configured to be electrically coupled to the stimulation generator such that electrical stimulation signals may be transmitted from the electrical stimulation generator to the electrode substrate via the lead wire and the contact substrate.

18. A medical device comprising:
a medical lead comprising
a lead body including an electrically conductive lead wire;
an electrical contact on a proximal portion of the lead body, the electrical contact comprising a contact substrate; and
an electrode on a distal portion of the lead body, the electrode comprising an electrode substrate,
wherein the electrode substrate is electrically coupled to the contact substrate via the electrically conductive lead wire,
wherein the lead wire is formed of a composition comprising titanium or titanium alloys,
wherein the electrode substrate is formed of a first beta-titanium alloy, and
wherein the contact substrate is formed of a second beta-titanium alloy, wherein the lead wire, the electrode substrate, and the contact substrate are formed of different compositions; and
a medical device including an electrical stimulation generator, wherein the medical lead is configured to be electrically coupled to the stimulation generator such that electrical stimulation signals may be transmitted from the electrical stimulation generator to the electrode substrate via the lead wire and the contact substrate.

* * * * *